(12) United States Patent
Tiao et al.

(10) Patent No.: US 9,117,149 B2
(45) Date of Patent: Aug. 25, 2015

(54) OPTICAL REGISTRATION CARRIER

(71) Applicant: Industrial Technology Research Institute, Hsinchu (TW)

(72) Inventors: Kuo-Tung Tiao, Hsinchu County (TW); Sheng-Li Chang, Hsinchu County (TW); Jung-Po Chen, Miaoli County (TW); Chun-Chieh Huang, Hsinchu (TW); Jyh-Chern Chen, New Taipei (TW); Rung-Ywan Tsai, Taoyuan County (TW); Tai-Ting Huang, Hsinchu (TW); Yuan-Chin Lee, Hsinchu (TW); Feng-Hsiang Lo, Hsinchu County (TW); Lung-Pin Chung, Miaoli County (TW); Hung-Chih Chiang, Chiayi (TW); Kuo-Yao Weng, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 106 days.

(21) Appl. No.: 13/947,100

(22) Filed: Jul. 21, 2013

(65) Prior Publication Data

US 2013/0299587 A1    Nov. 14, 2013

Related U.S. Application Data

(63) Continuation-in-part of application No. 13/646,026, filed on Oct. 5, 2012, now Pat. No. 8,514,390.

(60) Provisional application No. 61/721,035, filed on Nov. 1, 2012, provisional application No. 61/544,318, filed on Oct. 7, 2011.

(30) Foreign Application Priority Data

Jun. 13, 2012  (TW) .............................. 101121171 A

(51) Int. Cl.
G06K 19/06   (2006.01)
G06K 7/14    (2006.01)
(Continued)

(52) U.S. Cl.
CPC ...... *G06K 19/06084* (2013.01); *G01N 15/1434* (2013.01); *G02B 21/34* (2013.01);
(Continued)

(58) Field of Classification Search
USPC ......... 356/237.1–237.5, 246, 317; 250/208.1, 250/458.1, 459.1; 422/100; 235/470, 494
See application file for complete search history.

(56) References Cited

U.S. PATENT DOCUMENTS

| 3,946,367 A | 3/1976 | Wohlmut et al. |
| 4,183,614 A | 1/1980 | Feldman |

(Continued)

FOREIGN PATENT DOCUMENTS

| CA | 2341894 | 3/2000 |
| CN | 101223481 | 7/2008 |

(Continued)

OTHER PUBLICATIONS

"Office Action of Taiwan Counterpart Application", issued on Oct. 24, 2014, p. 1-10, in which the listed references were cited.
(Continued)

*Primary Examiner* — Sang Nguyen
(74) *Attorney, Agent, or Firm* — Jianq Chyun IP Office

(57) ABSTRACT

A carrier with the optical registration function is disclosed. The carrier allows the registration of inspected results of the sampling images of the sample to the corresponding address codes of the address coding site of the carrier.

18 Claims, 24 Drawing Sheets

(51) Int. Cl.
*G02B 21/34* (2006.01)
*G01N 15/14* (2006.01)
*G02B 21/00* (2006.01)
*G01N 35/00* (2006.01)
*G01N 15/10* (2006.01)

(52) U.S. Cl.
CPC ....... *G06K 7/1408* (2013.01); *G01N 35/00069* (2013.01); *G01N 2015/1006* (2013.01); *G01N 2015/1443* (2013.01); *G02B 21/0004* (2013.01)

(56) References Cited

U.S. PATENT DOCUMENTS

| | | | |
|---|---|---|---|
| 4,374,077 | A | 2/1983 | Kerfeld |
| 4,415,405 | A | 11/1983 | Ruddle et al. |
| 4,997,266 | A | 3/1991 | Mitchell |
| 5,175,030 | A | 12/1992 | Lu et al. |
| 5,446,521 | A | 8/1995 | Hainsey et al. |
| 5,486,924 | A | 1/1996 | Lacey |
| 5,726,970 | A | 3/1998 | Kaneko et al. |
| 5,761,187 | A | 6/1998 | Kaneko et al. |
| 5,766,677 | A | 6/1998 | Dimou et al. |
| 5,786,130 | A | 7/1998 | Hause et al. |
| 6,269,070 | B1 | 7/2001 | Kikuchi et al. |
| 6,399,936 | B1 | 6/2002 | Hang et al. |
| 6,511,788 | B1 | 1/2003 | Yasuda et al. |
| 6,594,006 | B1 | 7/2003 | Muehlhoff et al. |
| 6,734,442 | B1 | 5/2004 | Hause et al. |
| 6,993,173 | B2 | 1/2006 | Zuzan et al. |
| 7,052,841 | B2 | 5/2006 | Delenstarr |
| 7,133,543 | B2 | 11/2006 | Verwoerd et al. |
| 7,172,124 | B2 | 2/2007 | Wang et al. |
| 7,329,537 | B2 | 2/2008 | Qiu |
| 7,477,775 | B2 | 1/2009 | Oba et al. |
| 7,534,480 | B2 | 5/2009 | Ahn et al. |
| 7,711,410 | B2 | 5/2010 | Zavislan et al. |
| 7,751,046 | B2 | 7/2010 | Levy et al. |
| 7,982,188 | B2 | 7/2011 | Shinada et al. |
| 8,281,997 | B2 | 10/2012 | Moran et al. |
| 2002/0072122 | A1 | 6/2002 | Copeland et al. |
| 2002/0182117 | A1* | 12/2002 | Coassin et al. ............... 422/100 |
| 2003/0108985 | A1 | 6/2003 | Houtzager et al. |
| 2004/0026684 | A1 | 2/2004 | Empedocles |
| 2004/0131505 | A1* | 7/2004 | Koeda ......................... 422/100 |
| 2005/0208561 | A1 | 9/2005 | Rokutan et al. |
| 2005/0208685 | A1 | 9/2005 | Abdulhalim et al. |
| 2005/0264805 | A1* | 12/2005 | Cromwell et al. ............ 356/246 |
| 2006/0072807 | A1 | 4/2006 | Bultman et al. |
| 2006/0194205 | A1 | 8/2006 | Pouteau et al. |
| 2007/0099093 | A1 | 5/2007 | Zhang et al. |
| 2008/0139274 | A1 | 6/2008 | Imanaka et al. |
| 2010/0097696 | A1 | 4/2010 | Lin |
| 2011/0123398 | A1 | 5/2011 | Carrilho et al. |
| 2011/0308942 | A1 | 12/2011 | Liu et al. |
| 2011/0313684 | A1 | 12/2011 | Furrer et al. |
| 2012/0045087 | A1 | 2/2012 | Sun et al. |
| 2012/0162754 | A1 | 6/2012 | Liedtke |
| 2012/0243080 | A1 | 9/2012 | Hattori et al. |

FOREIGN PATENT DOCUMENTS

| | | |
|---|---|---|
| CN | 100498006 | 6/2009 |
| CN | 101809444 | 8/2010 |
| CN | 102226151 | 10/2011 |
| CN | 101702237 | 11/2011 |
| EP | 150384 | 3/1992 |
| EP | 492844 | 7/1992 |
| EP | 724730 | 8/1996 |
| EP | 1090291 | 4/2001 |
| EP | 1409127 | 4/2004 |
| EP | 1453963 | 9/2004 |
| EP | 1900827 | 3/2008 |
| GB | 1248564 | 10/1971 |
| JP | 11087223 | 3/1999 |
| JP | 2003294630 | 10/2003 |
| JP | 2004006725 | 1/2004 |
| JP | 2005063678 | 3/2005 |
| JP | 03670260 | 7/2005 |
| JP | 2005303083 | 10/2005 |
| JP | 03729843 | 12/2005 |
| JP | 2007305880 | 11/2007 |
| JP | 2011028291 | 2/2011 |
| JP | 04751328 | 8/2011 |
| JP | 04751353 | 8/2011 |
| JP | 04852600 | 1/2012 |
| JP | 2012003214 | 1/2012 |
| JP | 04974239 | 7/2012 |
| JP | 2013019900 | 1/2013 |
| KR | 1024956 | 3/2011 |
| KR | 20120059430 | 6/2012 |
| KR | 20120071302 | 7/2012 |
| TW | 200725794 | 7/2007 |
| TW | 201239776 | 10/2012 |
| TW | 201316331 | 4/2013 |
| WO | 9418883 | 9/1994 |
| WO | 9609599 | 3/1996 |
| WO | 2004031201 | 4/2004 |
| WO | 2006058187 | 6/2006 |
| WO | 2007076129 | 7/2007 |
| WO | 2012115635 | 8/2012 |
| WO | 2012137012 | 10/2012 |

OTHER PUBLICATIONS

D. J. Pritchard, et al, "A method for relocation of specified regions in tissue culture dishes", Cellular and Molecular Life Sciences, vol. 33, No. 8, 1977, pp. 1120.

P. Sandoz, et al., "Position referencing in optical microscopy thanks to sample holders with out-of-focus encoded patterns", Journal of Microscopy, vol. 225, Mar. 3, 2007, pp. 293-303.

Dominic St-Jacques, et al., "Nanoscale Grid Based Positioning System for Miniature Instrumented Robots", IEEE, Canadian Conference on Electrical and Computer Engineering (CCECE), 2003, vol. 3, May 4-7, 2003, pp. 1831-1834.

C.-L. Tsai, et al., "Alignment with sub-pixel accuracy for images of multi-modality microscopes using automatic calibration", Journal of Microscopy, vol. 232, 2008, pp. 164-176.

July A. Galeano Z., et al., "Position-referenced microscopy for live cell culture monitoring", Biomedical Optics Express, vol. 2, No. 5, May 1, 2011, pp. 1307-1318.

July A. Galeano Zea., et al., "Position-referenced microscopy: regions of interest localization and subpixel image comparison by means of pseudo-random patterns embedded in cell culture boxes", Proc. of SPIE-OSA Biomedical Optics, SPIE, vol. 7367, 2003, pp. 736707-1-736707-6.

* cited by examiner

| symbol | e1 | e2 | e3 | e4 | e5 |
|---|---|---|---|---|---|
| 1 | 1 | 0 | 0 | 0 | 1 |
| 2 | 0 | 1 | 0 | 0 | 1 |
| 3 | 1 | 1 | 0 | 0 | 0 |
| 4 | 0 | 0 | 1 | 0 | 1 |
| 5 | 1 | 0 | 1 | 0 | 0 |
| 6 | 0 | 1 | 1 | 0 | 0 |
| 7 | 0 | 0 | 0 | 1 | 1 |
| 8 | 1 | 0 | 0 | 1 | 0 |
| 9 | 0 | 1 | 0 | 1 | 0 |
| 0 | 0 | 0 | 1 | 1 | 0 |
| start | 0 | 0 | | | |
| end | 1 | 0 | | | |

OPTICAL REGISTRATION CARRIER

CROSS-REFERENCE

This application is a continuation-in-part application of and claims the priority benefit of U.S. patent application Ser. No. 13/646,026, filed Oct. 5, 2012, now pending. The prior application Ser. No. 13/646,026 claims the priority benefit of Taiwan application serial no. 101121171, filed on Jun. 13, 2012 and U.S. provisional application Ser. No. 61/544,318, filed on Oct. 7, 2011. This application also claims the benefits of provisional application Ser. No. 61/721,035, filed Nov. 1, 2012. The entirety of each of the above-mentioned patent applications is hereby incorporated by reference herein and made a part of this specification.

TECHNICAL FIELD

The disclosure relates in general to an assay component, and more particularly to an assay carrier with the optical registration function.

BACKGROUND

When one sample is inspected by optical method, the sampling points of the sample are normally consisted of many different and non-fixed points rather than one single point. Due to the absence of any regular feature points available on the sample for reference, the actual addresses of the sampling points may not be obtained by only using an open-loop motion method for sampling. Furthermore, if image capturing or signal detecting by using an optical scanning device equipped with a position feedback sensor, such as a laser galvo mirror equipped with a galvanometer or an optical encoder or a magnetic encoder, the position information of the optical scanning device is feedback. Then, the actual addresses of the sampling points on the sample are calculated by the feedback position information of the optical scanning device and the non-linear and complicated coordinate transformation formulas.

The said addresses of the sampling points are different and separated from the said feedback position information of the optical scanning device by a distance being far larger than the scale of the sampling displacement. Consequently, the position errors are amplified in the coordinate transformation, and result in differences between the calculated values and the actual addresses of the sampling points. Besides, for a live sample which needs to be periodically observed over a period of time, once the slide is removed from the equipment and then replaced to the equipment again, position change and image offset will occur.

SUMMARY

The disclosure is directed to an equipment with a sample inspecting device and an address detecting device. The equipment simultaneously obtains sample inspected information and its corresponding address information, so as to register each inspected result and its address of all the sampling points on the sample. Also, the disclosure provides a carrier with optical registration function, allowing registration of inspected results of the sampling points of the sample to the corresponding address codes of the address coding site of the carrier.

According to one embodiment, a carrier for carrying a sample is disclosed. The carrier includes a body of the carrier, an inspected site on the body and an address coding site. The sample is carried on the inspected site. The address coding site includes at least one coding micro-structure located in the body or located on the body, and a dimension of the coding micro-structure is at least less than 100 microns. A plurality of sampling images of the inspected site corresponds to a plurality of address codes of the address coding site. All of relative positions between each sampling image and its corresponding address code are the same.

According to another embodiment, a carrier for carrying a sample is disclosed. The carrier includes a plurality of inspected sites on a surface of the carrier and a plurality of address coding sites. The samples are carried on the plurality of inspected sites. The plurality of address coding sites and the plurality of inspected sites are arranged in alternation. A plurality of sampling images in each of the plurality of the inspected sites corresponds to a plurality of address codes in each of the plurality of the address coding sites. All of relative positions between each sampling image and its corresponding address code are the same.

According to another embodiment, an address registration method of a sample carrier having at least a address coding site and a sample inspected site is provided. A scanning beam is moved to aim at a target address coding sector of the address coding site. A sited address coding sector is scanned for decoding the sector barcode data of the sited address coding sector. Then, the decoded sector barcode is compared with a sector barcode of the target address coding sector; when the decoded sector barcode is not the same as the sector barcode of the target address coding sector, the scanning beam is moved to target sector by calculation; and when the decoded sector barcode is the same as the sector barcode of the target address coding sector, the target sector is scanned to generate clock signals for sampling the corresponding image signals of the sample in the inspected site and the corresponding images of the sample in the inspected site are captured. The capturing of the corresponding images of the sample in the inspected site is completed.

Figure 1:
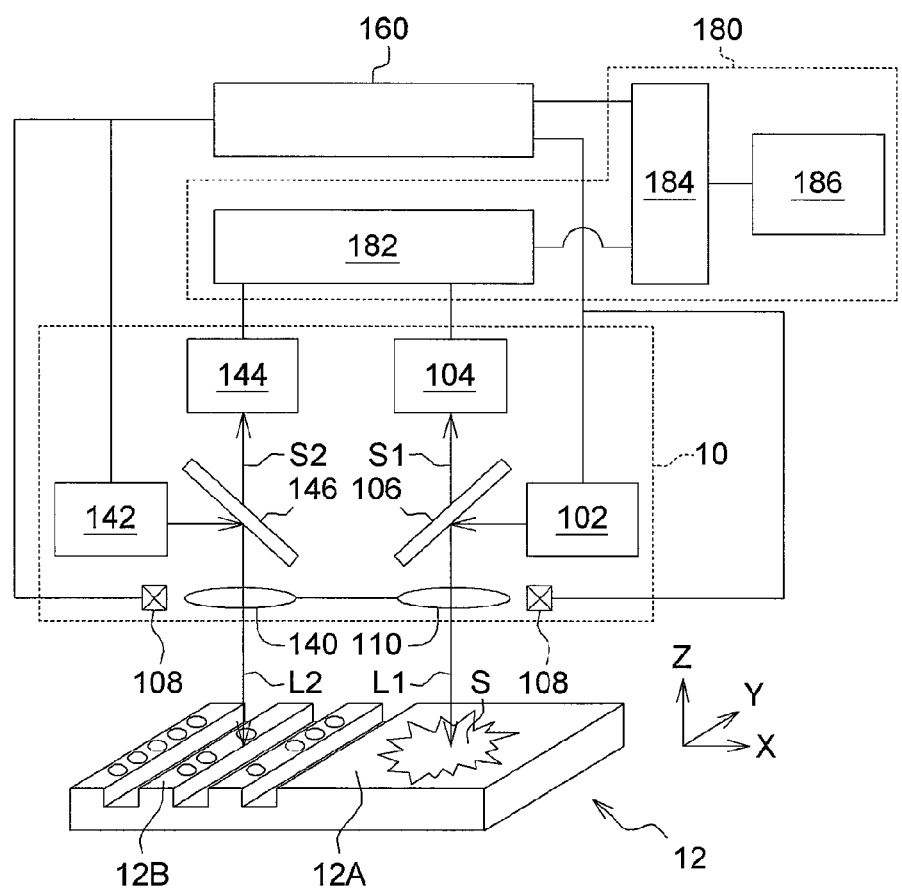
FIGS. 1~3 show schematic diagrams of an optical equipment according to different embodiments of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

Figure 2:
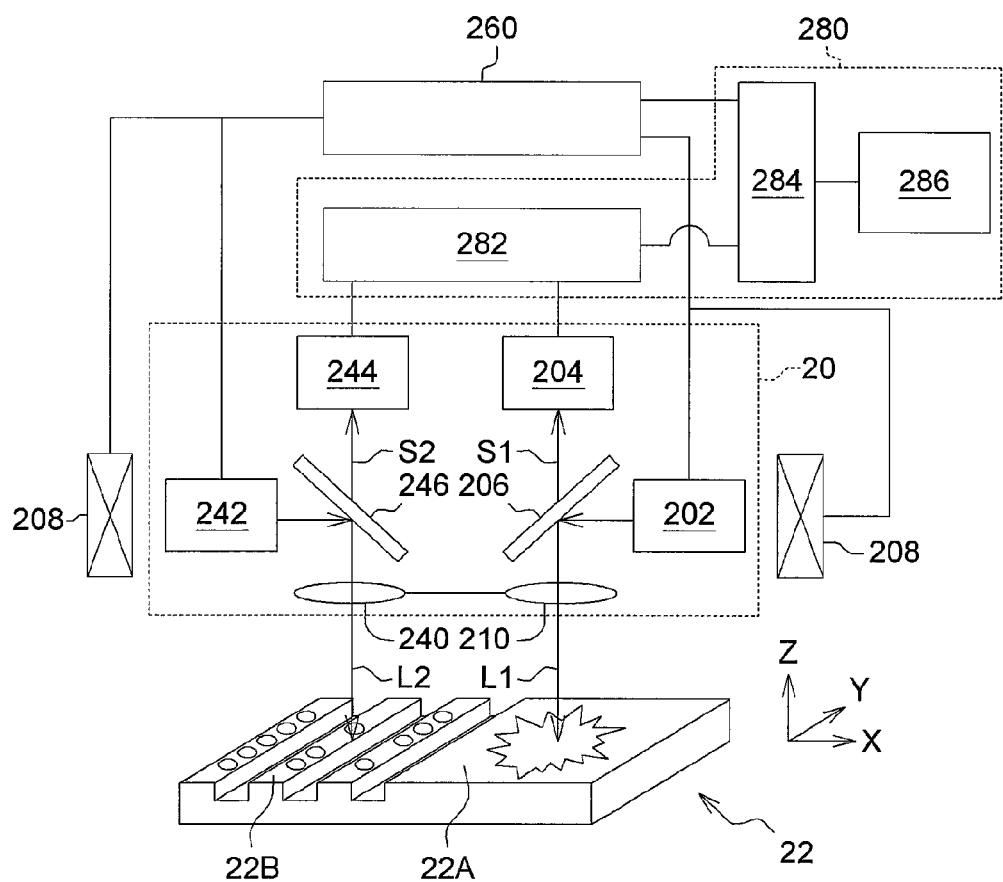
Figure 3:
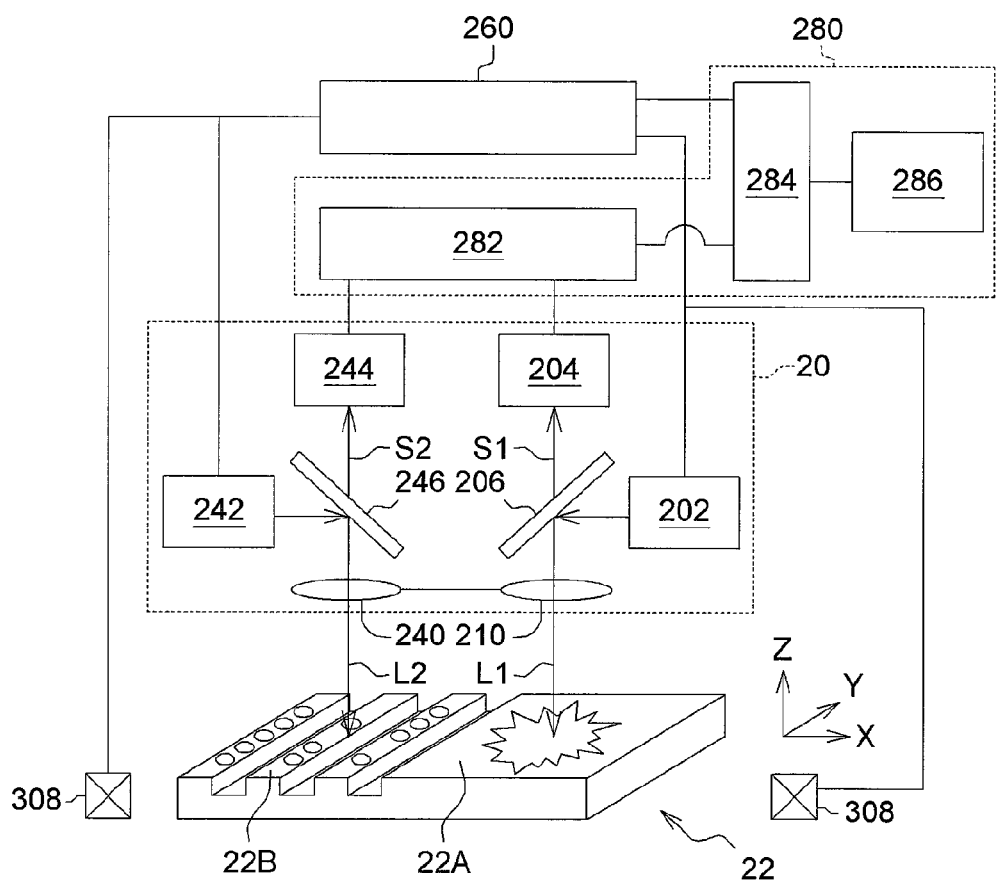

FIGS. 1~3 respectively show a schematic diagram of an optical equipment according to different embodiments of the disclosure. Referring to FIG. 1. The optical equipment 1 comprises an optical device 10, a controller 160 and a processing module 180. The controller 160 is such as a circuit comprising an actuator 108, and the controller 160 can be integrated within the processing module 180. The optical device 10 comprises a sample inspecting device and an address detecting device. The sample inspecting device comprises a first light source 102, a first detector 104, a first beam splitting element 106 and a first objective lens 110. The address detecting device comprises a second light source 142, a second detector 144, a second beam splitting element 146 and a second objective lens 140.

The optical equipment 1 may be used for inspecting an inspected specimen 12 having an inspected site 12A and an address coding site 12B. The specimen 12 includes the slide plate and the sample carried on the slide plate. In an embodiment, a sample S is placed on the inspected site 12A having several sampling points (not illustrated), and the address coding site 12B has several address codes (not illustrated). A beam of the first light source 102 is focused on the sample S by the first objective lens 110, and a beam of the second light source 142 is focused on the address coding site 12B by the second objective lens 140 simultaneously. The first beam splitting element 106 is such as a dichroic mirror. As indicated in FIG. 1, the first beam splitting element 106 may be used for reflecting the beam of the first light source 102 to the first objective lens 110 and then focusing the reflected beam on the inspected site 12A, and the second beam splitting element 146 may be used for reflecting the beam of the second light source 142 to the second objective lens 140 and then focusing the reflected beam on the address coding site 12B.

In an embodiment, the first light source 102 provides a beam having a first wavelength, the second light source 142 provides a beam having a second wavelength, and the first wavelength and the second wavelength may be the same or different, but the disclosure is not limited thereto. If the first wavelength and the second wavelength are the same, the first light source 102 and the second light source 142 may be integrated as one light source to save space and cost. If the first wavelength and the second wavelength are not the same, then respective light sources with suitable wavelengths are provided according to the features of the inspected site 12A and the address coding site 12B. For example, if the sample is a biological sample with a fluorescent mark, then the first wavelength of the first light source 102 must be a specific wavelength capable of exciting the said fluorescent mark. The first wavelength of the first light source 102 may not be suitable for detecting the address coding site 12B. Therefore, the first light source 102 and the second light source 142 may be applied in a wider range of inspection and address coding by using independent light sources.

In the present embodiment, the address coding site comprises address codes having different reflective indexes or optical polarization directions. As indicated in FIG. 1, the controller 160 controls the first beam L1 of the first light source 102 to be focused on different sampling points of the sample S and then correspondingly generates several first optical signals S1, which may be transmitted to the first detector 104 through the first beam splitting element 106. Moreover, the controller 160 may control the second beam L2 of the second light source 142 to be focused on those corresponding address codes of the address coding site 12B and then correspondingly generates several second optical signal S2, which may be transmitted to the second detector 144 through the second beam splitting element 146.

In the present embodiment, the actuator 108 is disposed near the first objective lens 110 and the second objective lens 140 for receiving commands from the controller 160 to control the movements of the first objective lens 110 and the second objective lens 140. The relative positions between the first objective lens 110 and the second objective lens 140 are fixed, so that the first objective lens 110 and the second objective lens 140 are displaced with respect to the specimen 12, and several sample inspected information and its corresponding address information can thus be obtained. It is noted that there is a fixed relative position between each sampling point on which the first beam L1 is focused and the address code on which its corresponding second beam L2 is focused. The controller 160 controls the first objective lens 110 and the second objective lens 140 to move their focusing positions simultaneously, and the fixed relative position still does not change. The processing module 180 may obtain the registered image or signal information of the specimen according to the first optical signals S1 and the second optical signals S2.

As indicated in FIG. 1, the processing module 180 may comprise a processing unit 182, a calculator 184 and a storage unit 186. The processing unit 182, coupled to the first detector 104 and the second detector 144, is realized by such as a microprocessor or a processor. The calculator 184 is realized by such as a computer or a central processing unit (CPU). The storage unit 186 is realized by such as a memory, a magnetic tape, a magnetic disc or an optical disc. The storage unit 186 is selectively disposed on and coupled to the calculator 184.

In the present embodiment, the calculator 184 commands the controller 160 to adjust the focusing positions of the first objective lens 110 and the second objective lens 140. Furthermore, the controller 160 controls the scan path of the first beam L1 of the first light source 102 to pass through the sampling points, so that the first beam L1 focusing on the sampling points is reflected as the first optical signals S1. Meanwhile, the controller 160 controls the scan path of the second beam L2 of the second light source 142 to pass through the address codes, so that the second beam L2 focusing on the address codes is reflected as the second optical signals S2. After that, the processing unit 182 receives the first optical signals S1 and the second optical signals S2. Since the relative position between each sampling point and its corresponding address code is fixed, a sample inspected result may be generated according to the received first optical signals S1, and an address of the corresponding sampling point may be generated according to the received second optical signals S2. Then, the calculator obtains the registered image or signal information of the specimen according to the said inspected result and its address information. The storage unit 186 may receive and store the registered image or signal information.

Referring to FIG. 2, the optical equipment 2 comprises an optical device 20, a controller 260 and a processing module 280. The controller 260 is such as a circuit comprising the actuator 208, and the controller 260 can be integrated within the processing module 280. The optical device 20 comprises a sample inspecting device and an address detecting device. The sample inspecting device comprises a first light source 202, a first detector 204, a first beam splitting element 206 and a first objective lens 210. The address detecting device comprises a second light source 242, a second detector 244, a second beam splitting element 246 and a second objective lens 240.

The optical equipment 2 may be used for inspecting a specimen 22 having an inspected site 22A and an address coding site 22B. The processing module 280 may comprise a processing unit 282, a calculator 284 and a storage unit 286. The processing unit 282 is coupled to the first detector 204 and the second detector 244. The elements and method of the optical equipment 2 for inspecting the specimen 22 are similar to that of the optical equipment 1 except that the controller 260 is used for controlling the movement of the entire optical device 20, so that the optical device 20 is displaced with respect to the specimen 22 and several sample inspected results and their addresses can thus be obtained. The controller 260 controls the actuator 208 to move the entire optical device 20, such that the entire optical device 20 can be moved along a direction perpendicular to the optical axis of the first beam L1 of the first light source 202 and along a direction parallel to the optical axis of the first beam L1 of the first light source 202, for scanning the specimen 22. Then, the processing module 280 obtains the sample inspected results and their corresponding address information of the specimen 22 according to the first optical signals S1 and the second optical signals S2.

Referring to FIG. 3, the optical equipment 3 comprises an optical device 20, a controller 260 and a processing module 280. The optical equipment 3 is similar to the optical equipment 2. The same elements between the optical equipment 2 and the optical equipment 3 are represented by same reference numbers, and the similarity is not repeated here. A difference between the optical equipment 3 in FIG. 3 and the optical equipment 2 in FIG. 2 is that the actuator 308 is used for controlling the specimen 22 so that the specimen 22 can be moved along a direction perpendicular to the optical axis of the first beam L1 of the first light source 202 and along a direction parallel to the optical axis of the first beam L1 of the first light source 202.

Figure 4:
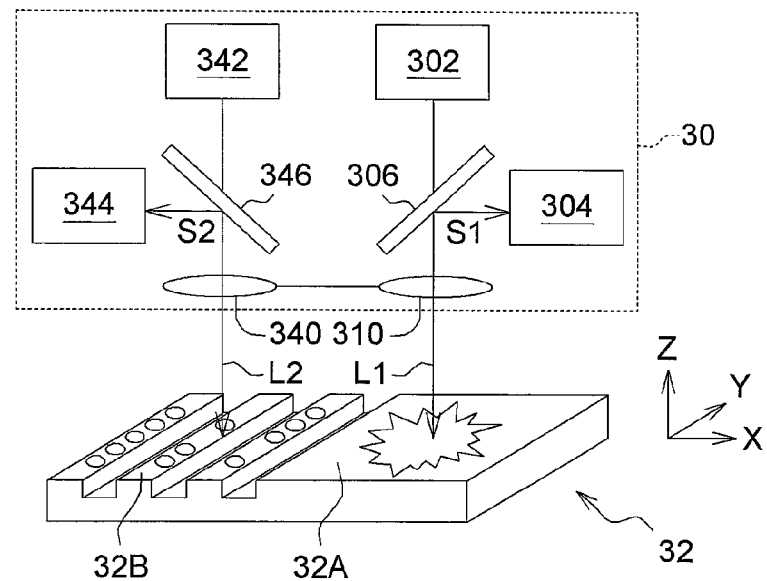
FIGS. 4~9 show schematic diagrams of an optical device and an inspected specimen according to different embodiments of the disclosure.

FIGS. 4~9 respectively show a schematic diagram of an optical device and an inspected specimen according to different embodiments of the disclosure. Referring to FIG. 4. The optical device 30 comprises a sample inspecting device and an address detecting device. The sample inspecting device comprises a first light source 302, a first detector 304, a first beam splitting element 306 and a first objective lens 310. The address detecting device comprises a second light source 342, a second detector 344, a second beam splitting element 346 and a second objective lens 340. The optical device 30 may replace the optical device 10 or the optical device 20 in the optical equipment 1~3.

The optical equipment of the optical device 30 may be used for inspecting a specimen 32 having an inspected site 32A and an address coding site 32B. The elements and method of the optical device 30 for inspecting the specimen 32 are similar to that of the optical devices 10 and 20 except that in the optical device 30, the position of the first light source 302 swaps with that of the first detector 304 and the position of the second light source 342 swaps with that of the second detector 344. Therefore, the transmission paths of the first optical signals S1 and the second optical signals S2 are different from that of the optical device 10 of FIG. 1 and the optical device 20 of FIG. 2~3.

Figure 5:
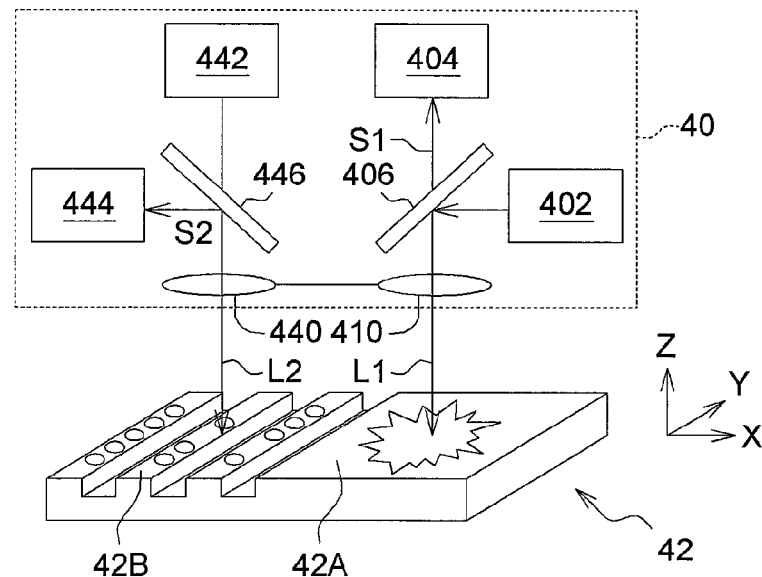

Referring to FIG. 5. The optical device 40 comprises a sample inspecting device and an address detecting device. The sample inspecting device comprises a first light source 402, a first detector 404, a first beam splitting element 406 and a first objective lens 410. The address detecting device comprises a second light source 442, a second detector 444, a second beam splitting element 446 and a second objective lens 440. The optical device 40 may replace the optical device 10 or the optical device 20 in the optical equipment 1~3.

The optical equipment of the optical device 40 may be used for inspecting a specimen 42 having an inspected site 42A and an address coding site 42B. The elements and method of the optical device 40 for inspecting the specimen 42 are similar to that of the optical device 30 except that in the optical device 40, the position of the first light source 402 swaps with that of the first detector 404. Therefore, the transmission path of the first optical signals S1 is different from that of the optical device 30 of FIG. 4.

Figure 6:
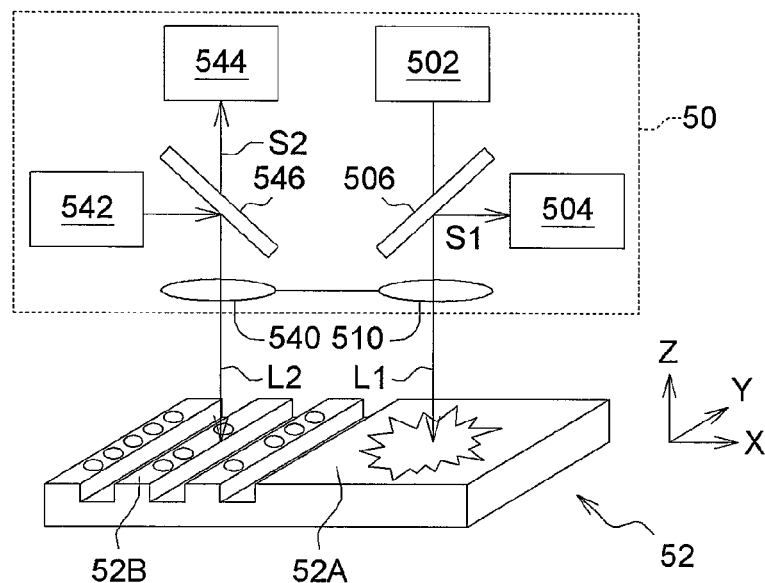

Referring to FIG. 6. The optical device 50 comprises a sample inspecting device and an address detecting device. The sample inspecting device comprises a first light source 502, a first detector 504, a first beam splitting element 506 and a first objective lens 510. The address detecting device comprises a second light source 542, a second detector 544, a second beam splitting element 546 and a second objective lens 540. The optical device 50 may replace the optical device 10 or the optical device 20 in the optical equipment 1~3.

The optical equipment of the optical device 50 may be used for inspecting a specimen 52 having an inspected site 52A and an address coding site 52B. The elements and method of the optical device 50 for inspecting the specimen 52 are similar to that of the optical device 30 except that in the optical device 50, the position of the second light source 542 swaps with that of the second detector 544. Therefore, the transmission path of the second optical signals S2 is different from that of the optical device 30 of FIG. 4.

Figure 7:
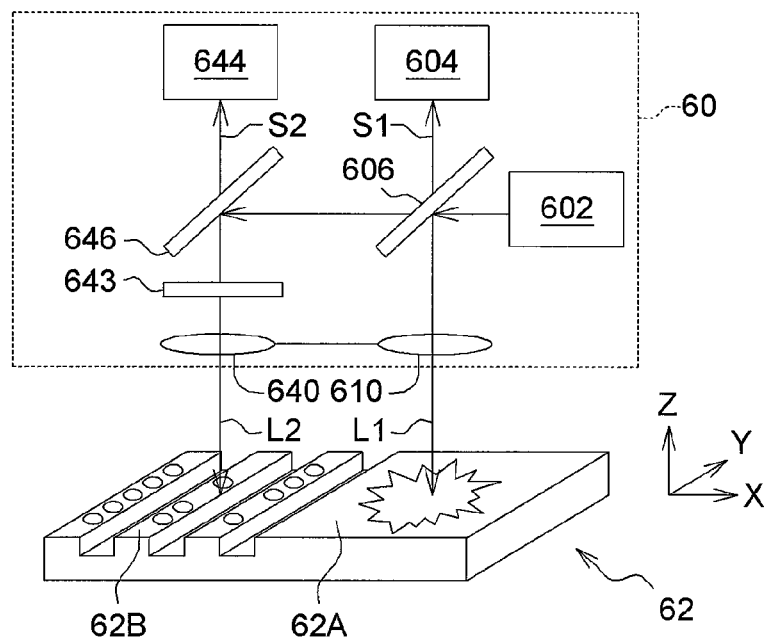

Referring to FIG. 7, the optical device 60 comprises a sample inspecting device and an address detecting device. The sample inspecting device comprises a first light source 602, a first detector 604, a first beam splitting element 606 and a first objective lens 610. The address detecting device comprises a second detector 644, a second beam splitting element 646 and a second objective lens 640. The optical device 60 may replace the optical device 10 or the optical device 20 in the optical equipment 1~3.

The optical equipment of the optical device 60 may be used for inspecting a specimen 62 having an inspected site 62A and an address coding site 62B. The elements and method of the optical device 60 for inspecting the specimen 62 are similar to that of the optical devices 10 and 20 except that the optical device 60 only has a first light source 602 and the second light source is omitted. That is, the first light sources 102 and 202 and the second light sources 142 and 242 of the optical device 1020 of FIGS. 1~3 are integrated as one single first light source 602 for saving both space and costs. In the present embodiment, the second beam splitting element 646 is realized by such as a polarization beam splitter (PBS), and a one-quarter wavelength plate 643 is disposed between the second beam splitting element 646 and the second objective lens 640 for increasing the energy efficiency in transmitting the second optical signal S2 to the second detector 644.

Figure 8:
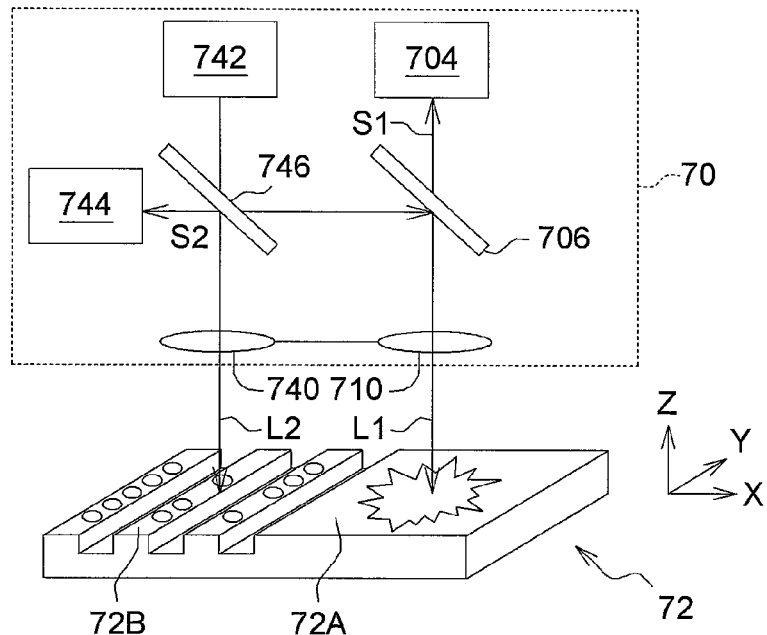

Referring to FIG. 8. The optical device 70 comprises a sample inspecting device and an address detecting device, and the sample inspecting device comprises a first detector 704, a first beam splitting element 706 and a first objective lens 710. The address detecting device comprises a second light source 742, a second detector 744, a second beam splitting element 746 and a second objective lens 740. The optical device 70 may replace the optical device 10 or the optical device 20 in the optical equipment 1~3.

The optical equipment of the optical device 70 may be used for inspecting a specimen 72 having an inspected site 72A and an address coding site 72B. The elements and method of the optical device 70 for inspecting the specimen 72 are similar to that of the optical devices 10 and 20 except that the optical device 70 only has a second light source 742 and the first light source is omitted. That is, the first light sources 102 and 202 and the second light sources 142 and 242 of the optical device 10~20 of FIGS. 1~3 are integrated as one single second light source 742 for saving both space and costs.

Figure 9:
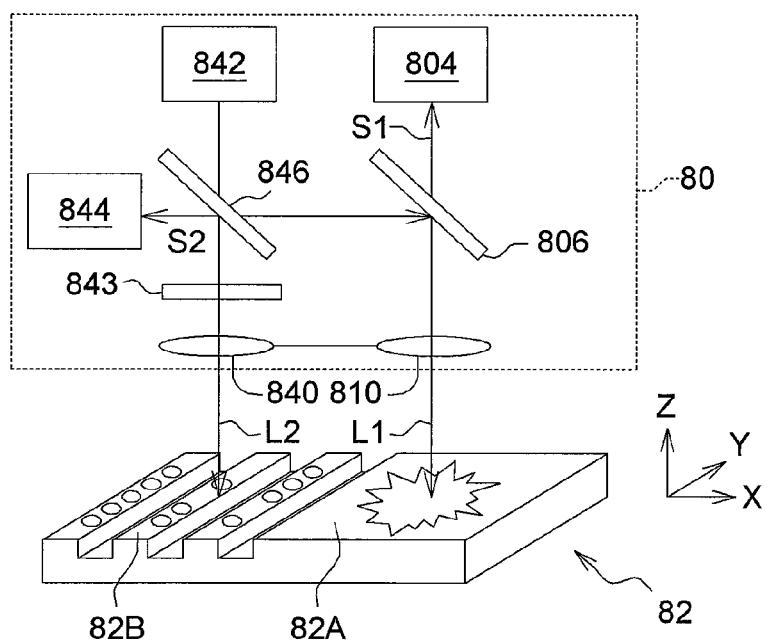

Referring to FIG. 9, the optical device 80 comprises a sample inspecting device and an address detecting device. The sample inspecting device comprises a first detector 804, a first beam splitting element 806 and a first objective lens 810. The address detecting device comprises a second light source 842, a one-quarter wavelength plate 843, a second detector 844, a second beam splitting element 846 and a second objective lens 840. The optical device 80 may replace the optical device 10 or the optical device 20 in the optical equipment 1~3.

The optical equipment of the optical device 80 may be used for inspecting a specimen 82 having an inspected site 82A and an address coding site 82B. The elements and method of the optical device 80 for inspecting the specimen 82 are similar to that of the optical devices 10 and 20 except that the optical device 80 only has a second light source 842 and the first light source is omitted for saving both space and costs. In the present embodiment, the second beam splitting element 846 is realized by such as a polarization beam splitter (PBS), and the one-quarter wavelength plate 843 is disposed between the second beam splitting element 846 and the second objective lens 840 for increasing the energy efficiency in transmitting the second optical signal S2 to the second detector 844.

Figure 10A:
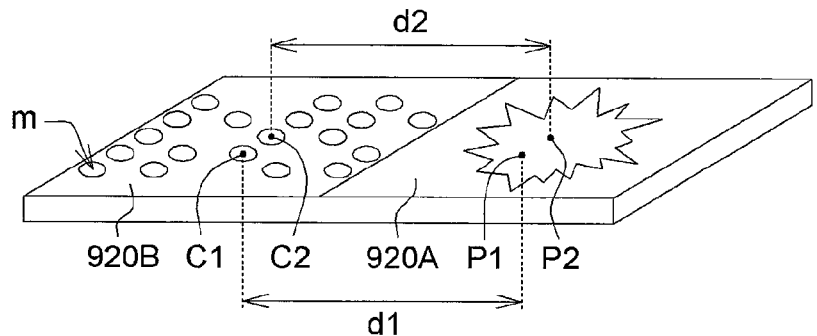
FIGS. 10A~10D show schematic diagrams of an inspected specimen according to different embodiments of the disclosure.

FIG. 10A~10D show schematic diagrams of a specimen according to different embodiments of the disclosure. The specimens 92-1~92-4 each having inspected sites 920A~926A and address coding sites 920B~926B may be used in the optical devices 10~80 of any embodiments of the disclosure. Referring to FIG. 10A, several address codes C1~C2 of the address coding site 920B of the specimen 92-1 respectively correspond to several micro-structures m, and may be realized by such as several pits arranged according to an arrangement associated with address encoding. Furthermore, when the focusing point of the first light source is moved to the sampling point P2 from the sampling point P1, the focusing point of the second light source is correspondingly moved to the address code C2 from the address code C1, and the distance d1 between the sampling point P1 and the address code C1 is equal to the distance d2 between the sampling point P2 and the address code C2.

Figure 10B:
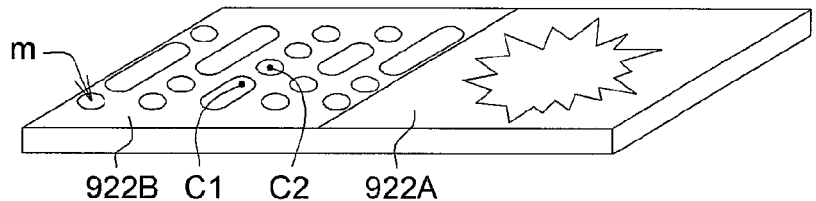
Figure 10C:
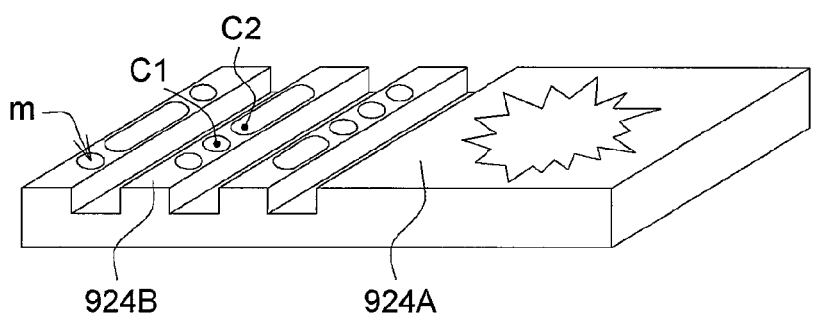
Figure 10D:
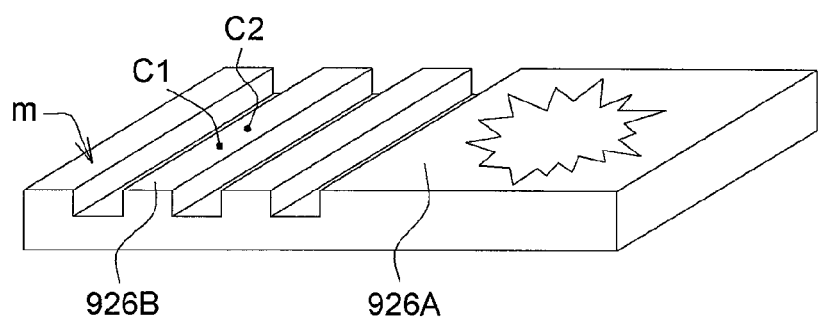

Referring to FIG. 10B. The specimen 92-2 is similar to the specimen 92-1 except that the micro-structures m corresponding to the address codes C1~C2 are realized by pits and long pits arranged in a specific manner. The micro-structures m may also be realized by holes of any shapes (not illustrated), and the disclosure is not limited thereto. Referring to FIG. 10C. The micro-structures m corresponding to the address codes C1~C2 may also be mixed with several tracks and pits (including pits or long pits) or holes of any shapes (not illustrated). Referring to FIG. 10D. The micro-structures m corresponding to the address codes C1~C2 may also be realized by several tracks each having several coding structures or address coding information.

In another embodiment, the address codes C1~C2 may also correspond to several address coding features having different reflective indexes or optical polarization directions. In other words, the address codes C1~C2 do not have to correspond to the micro-structures of FIG. 10A~10D as long as the beam may radiate the address codes C1~C2 to generate signals having different light intensities. In other words, any arrangement of the address codes allowing the beam focused on different address codes to be reflected as several optical signals whose energy levels are different would do.

Figure 11:
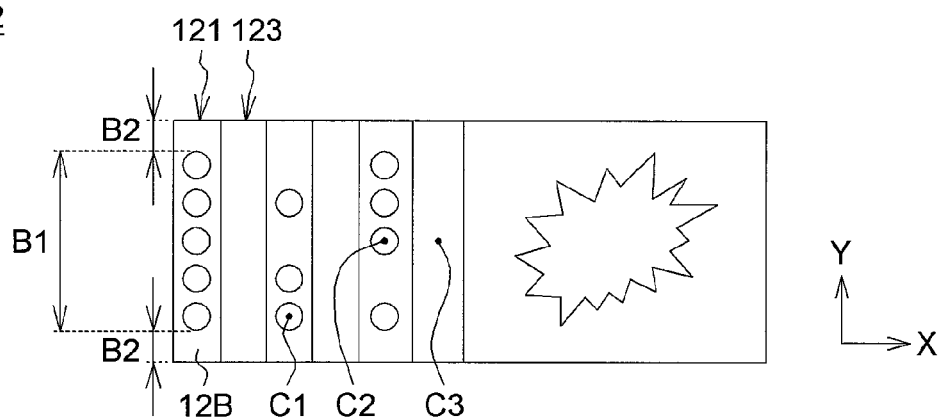
FIG. 11 shows a top view of an inspected specimen according to an embodiment of the disclosure.

FIG. 11 shows a top view of a specimen according to an embodiment of the disclosure. The method for inspecting the specimen 12 by the optical equipment 1 is elaborated below with the exemplification of the optical equipment 1 of FIG. 1. Referring to both FIG. 1 and FIG. 11. The specimen 12 (such as a test slide) has an address coding site 12B having several address codes C1~C3 and corresponds to the grooves 123 and the lands 121 having several micro-structures. The controller 160 controls the second beam L2 of the second light source 142 to scan the address coding structure of respective groove 123 and land 121 so as to obtain the address coding information. Moreover, the controller 160 controls the beam to cross over the grooves 123 and the lands 121 to perform scanning to obtain a track counting information.

In an embodiment, different address coding structures are disposed on respective grooves 123 and lands 121 of the address coding site 12B according to the encoding method. The address coding structures on each track are distributed in the block B1 along the Y-axis direction (that is, the track direction of the groove 123 and the land 121) of the specimen 12, wherein the block B2 on the two ends of the track do not have any coding structures disposed thereon.

Figure 12:
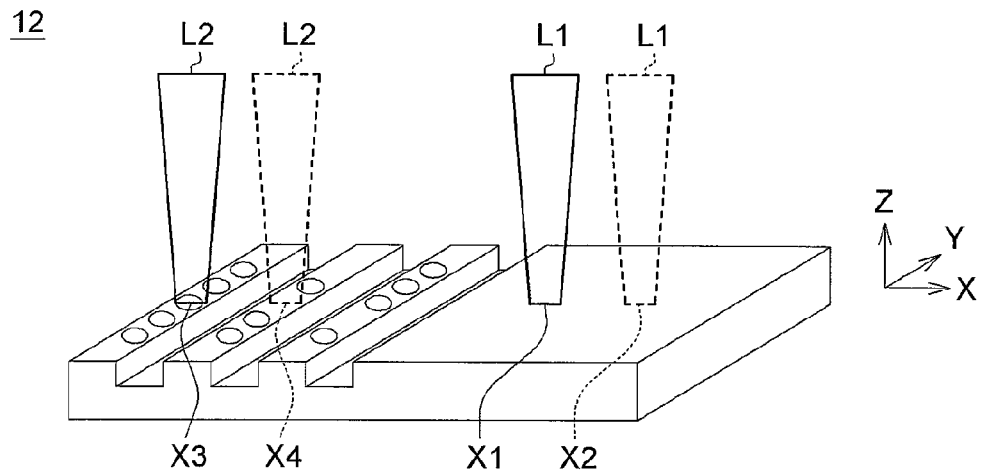
FIG. 12 shows a schematic diagram of a second beam being focused on different address codes of the address coding site of an inspected specimen according to an embodiment of the disclosure.

FIG. 12 shows a schematic diagram of a second beam being focused on different positions of a specimen 12 according to an embodiment of the disclosure. As indicated in FIG. 12, when the first beam L1 is moved to the second position X2 from the first position X1 and the second beam L2 is correspondingly moved to the fourth position X4 from the third position X3, the distance between the first position X1 and the third position X3 is equal to the distance between the second position X2 and the fourth position X4.

Figure 13:
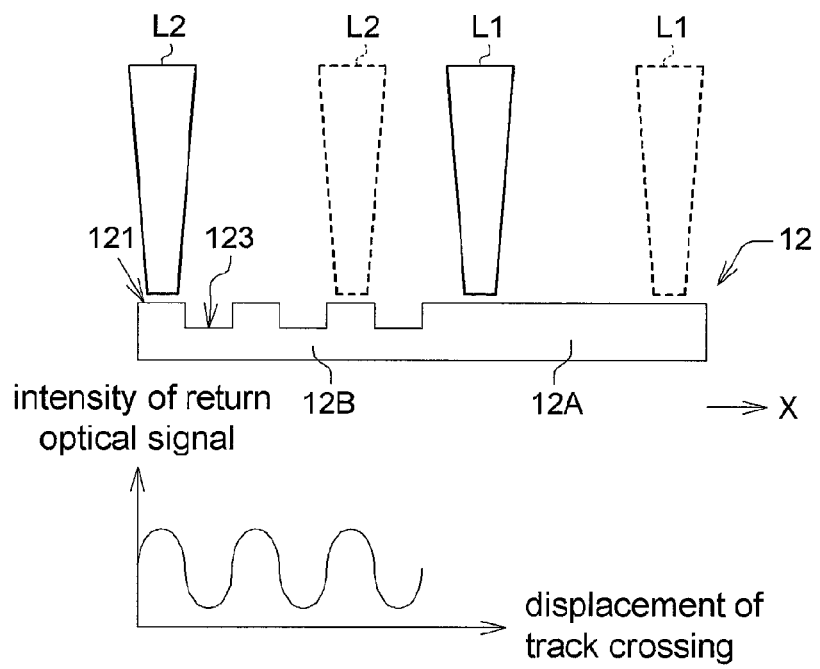
FIG. 13 shows a schematic diagram of the intensity of a second optical signal corresponding to a second beam being focused on the block B2 of FIG. 11 and crossing over different tracks.

FIG. 13 shows a schematic diagram of the intensity of a second optical signal corresponding to a second beam L2 being focused on the block B2 of FIG. 11 and crossing over different tracks along the X-axis direction of the specimen 12. Referring to FIG. 13. The second beam L2 is focused on the block B2 and crosses over different tracks along the X-axis direction of the specimen 12. When the second beam L2 is focused on the land 121, the light intensity, which denotes the track information and is detected by the second detector 144 (illustrated in FIG. 1), generates signals having strongest intensity. When the second beam L2 is focused on the groove 123 between two adjacent lands 121, the light intensity, which denotes the track information and is detected by the second detector 144, generates signals having weakest intensity. Based on the difference in the light intensity denoting the track information, the track position on which the second beam L2 is focused may be estimated. Based on the count of the wave patterns of the light intensities denoting the track crossing information, the number of tracks being crossed over can be estimated. Furthermore, during the scanning process (for example, the second beam L2 is moved along the Y-axis direction of the specimen 12), the light intensity denoting the track information may maintain at the strongest or the weakest level by method of servo control (is realized by such as push-pull method or differential phase detection method well-known in optical storage). Thus, the specific position of the groove and the land being scanned can be obtained, and accurate addressing information can be obtained through decoding by determining the address coding structure on the track.

Figure 14:
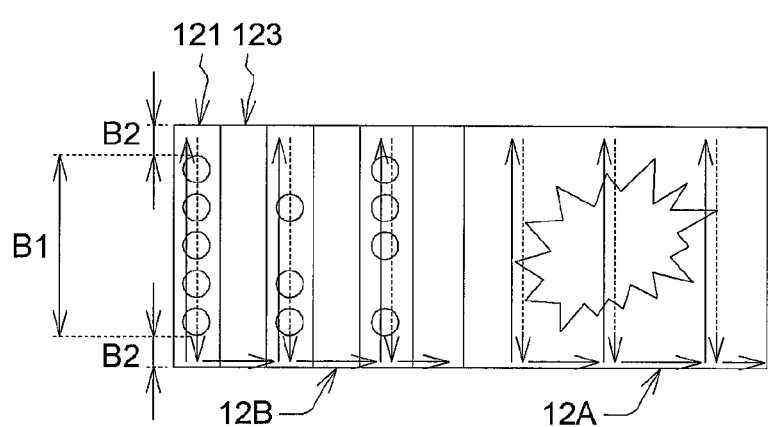
FIGS. 14~15 shows schematic diagrams of a scan path of an optical equipment according to different embodiments of the disclosure.
Figure 15:
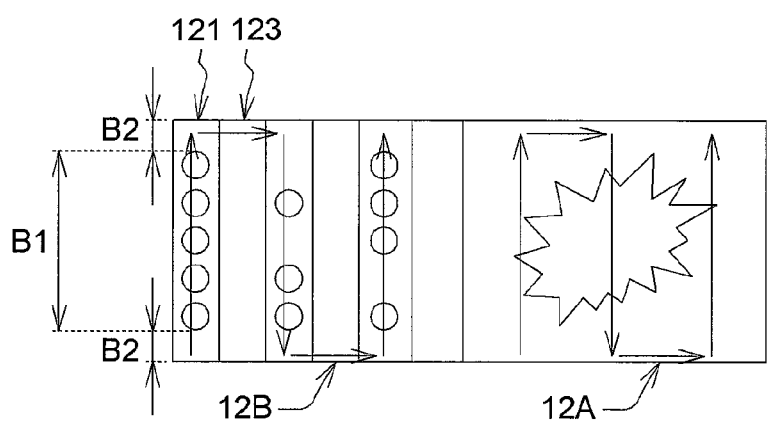

FIGS. 14~15 respectively show a schematic diagram of a scan path of an optical equipment according to different embodiments of the disclosure. Referring to FIG. 14. The second beam L2 scans from one end of the groove or land of the address coding site 12B to the other end, returns by following the original path, and crosses the track in the block B2 of the address coding site 12B. Then, the above scanning process is repeated. Referring to FIG. 15. The second beam L2 alternatively scans from one end of the groove or land of the address coding site 12B to the other end, crosses the track on the block B2 of the address coding site 12B, and scans from one end of the address encoding track to the other end in an opposite direction. Then, the above S-shaped track crossing and scanning are repeated.

In the present embodiment, the specimens 12-1 and 12-2 may be scanned according to a scan path along the land structure or the groove structure of the address coding site 12B. Also, the interval between the grooves or between the lands of the address coding site 12B may be reduced so as to increase the scan resolution (that is, the density of image or signal sampling points of the sample inspected site 12A of the specimen 12). Alternatively, the address coding structures may be distributed over both the grooves and lands of the address coding site 12B of FIGS. 14~15. Meanwhile, the scan resolution will be two times higher than that of the address coding site 12B illustrated in FIGS. 14~15.

Figure 16:
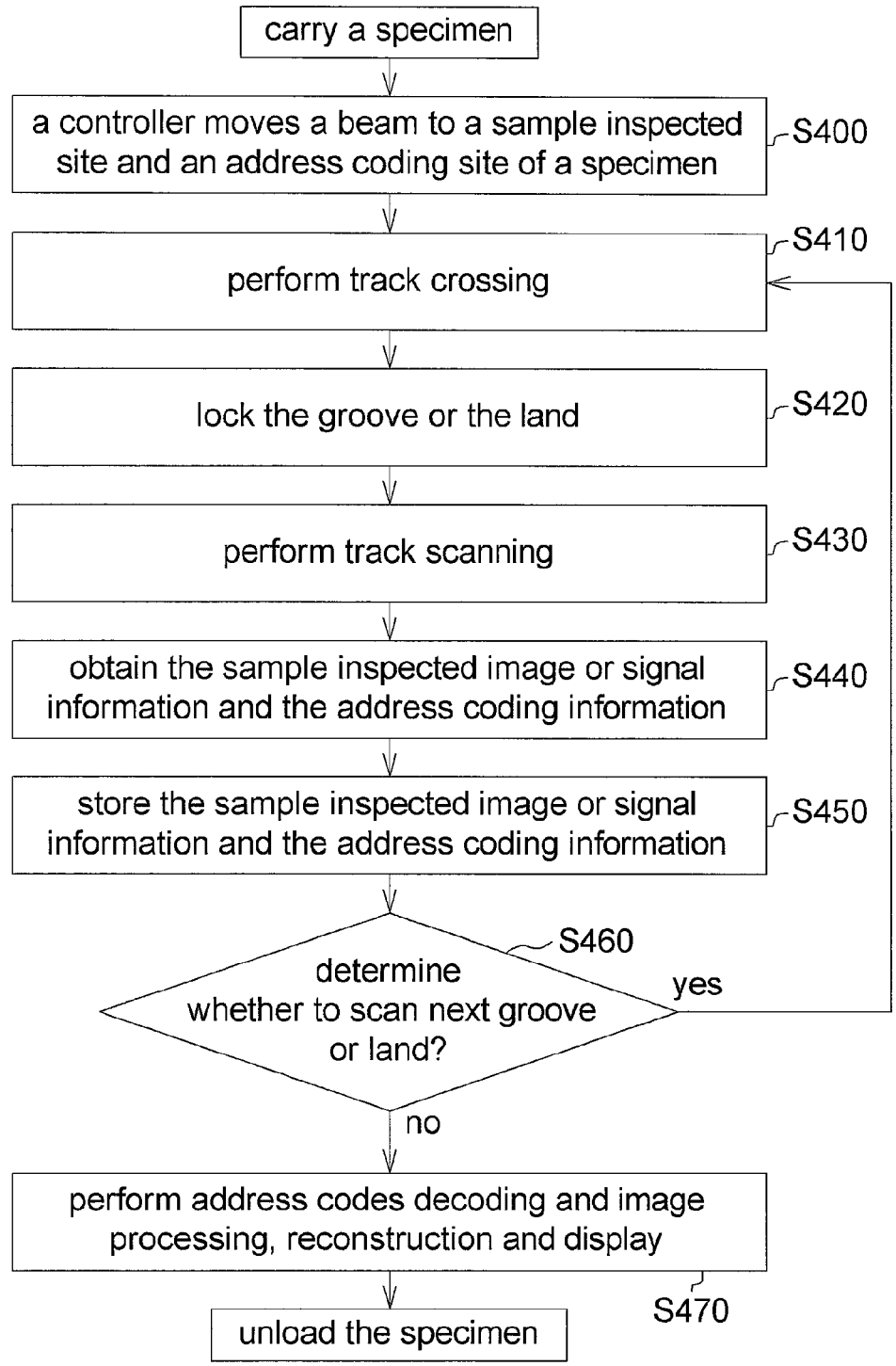
FIG. 16 shows a flowchart of an address registration method according to an embodiment of the disclosure.

FIG. 16 shows a flowchart of an address registration method according to an embodiment of the disclosure. Firstly, a specimen is carried. Next, the method proceeds to step S400, a beam is moved to a sample inspected site and an address coding site of a specimen by a controller. Then, the method proceeds to step S410, track crossing is performed. Then, the method proceeds to step S420, the groove or the land is locked. After that, the method proceeds to step S430, a track scanning process is performed. Afterwards, the method proceeds to step S440, the sample inspected image or signal information and the address coding information are obtained. Then, the method proceeds to step S450, the sample inspected image or signal information and the address coding information are stored. Then, the method proceeds to step S460, whether to scan next groove or land is determined. If so, the method returns to step S410, otherwise, the method proceeds to step S470, address codes decoding and image processing, reconstruction and display are performed. Lastly, the specimen is unloaded. FIG. 16 only shows a flowchart of an address registration method according to an embodiment of the disclosure. However, the above disclosed embodiments of the disclosure are also applicable to the address registration method, and the disclosure is not limited thereto.

An optical equipment and an address registration method are disclosed in above embodiments of the disclosure. A beam is focused on a sample placed on an inspected site of a specimen for capturing an image or detecting a signal, and another beam is focused on the address coding site adjacent to the inspected site to obtain address coding information. Since the two beams are adjacent and synchronized, the inspected image or signal of each sampling point has corresponding address code, such that the image or signal denoted by the sample inspected information has addressing features. Besides, the sampling point can be any position, and images can be captured and signals can be detected on several different sampling points. Furthermore, random noises can be eliminated by taking average on the values detected on the same position so as to produce a result with high signal to noise (S/N) ratio. Or, under the circumstance that the signal is feeble, a result with sufficient intensity and free of position offset can be obtained through the integral over the time. Without reducing the resolution level, several small-area images can be stitched to form one large-area image by way of address registration.

Since the two beams focused on the inspected site and the address coding site are adjacent and synchronized, a simple and linear position relationship is formed between the position of the actual sampling point and the address obtained by detecting and decoding the optical signal reflected from the beam of the address coding site and, smaller error accumulation and higher positioning precision are thus achieved. Since the inspected site and the address coding site are on the same specimen or slide (carrying container) at the same time, the inspection is traceable, repeatable, and free of image offset despite that the specimen or slide is removed from the original inspecting equipment in the course of detection and is placed back latter. This feature is very convenient for dynamic comparison of the specimen over the time, and for image or signal processing as well. Apart from being used in optical inspection, the optical equipment of the above embodiments of the disclosure may also be used in other optical operations such as optical therapy, optical tweezers and so on for providing accurate positioning required in the operating process.

Additionally, the above-mentioned address codes may be designed with address coding structures or micro-structures by taking advantages of the encoding principles of the barcode or compact discs. That is, the address codes can be obtained by decoding (or reading) the codes or data stored by the address coding micro-structures and the address coding micro-structures may cause differences in optical signals as barcodes or compact discs.

The barcode is a medium with storage capacity, composed of rectangular black lines with different thickness (usually in the millimeter range changes) and blank lines parallel to the black lines. Regardless of the barcodes of different encoding principles, the barcode basically consists of four parts: (i) start code, (ii) data code, (iii) check code to ensure data accuracy and (iv) end code. For example, for the barcode of code 39 (code 3 of 9), each character is composed of a total of nine lines of five black lines (i.e. bar) and 4 white (blank) lines (i.e. space), and three lines of the five black lines are thick lines. Taking advantage of the reflectance differences between the black lines (low reflectance) and white lines (high reflectance) using light scanning the nine lines, the optical reading device (usually a laser or CCD scanner) produce pulses of different time widths, which are used to tell the numbers of the bits and to interpret the message of the barcode.

Compact disc is another medium with huge storage capacity. The recording principle of compact discs utilizes the pits distributed in a spiral pattern on the polycarbonate substrate of the disc to record information or data. The recorded data can be read using laser light focused by the objective lens to scan the disc surface. The differences in the reflected light intensity of the focused laser light irradiated on the recording region and on the non-recording region are used to determine changes in the pits, which are interpreted into data. The light reflected from the disc will finally impinge onto the detector. Here, generally a quadrant detector is used. The optical signals will then be transferred into electric signals by the detector. The focusing and tracking error information's can be further obtained from mathematical manipulation using these electric signals on each divisions of the quadrant detector. The focusing error signal (FES) is generally produced from the astigmatic focusing detection method by subtracting the sum of signals of two diagonal divisions by that of the other two diagonal divisions in another orientation. The. Concerning the tracking error signal (TES), one of the most popular methods is the "push-pull method". It is used especially for producing the TES of a re-writable or a recordable disc. When the focused light beam output from the objective lens of the optical pickup head is incident on the land-groove structure of the disc, the reflected beams will include the 0 order, −1 order, +1 order and higher order beams due to the land-groove structure on the disc. This land-groove structure performs just like a grating. But, since the limited numerical aperture of the objective lens, only the 0 order, and some part of the −1 order, and +1 order beams can be collected by the objective lens. The reflected light beams will be projected on the quadrant detector, and the −1 order beam and the +1 order beam will interference with the 0 order beam due to different phases between them. Generally, the light beam of the −1 order will impinge onto two neighboring divisions of the quadrant detector, while the light beam of the +1 order will impinge onto the other two neighboring divisions of the quadrant detector. If the signal differences of these two parts is called "push-pull signal". The sum of the total signals on the quadrant detector is called the "cross-track signal". For the other optical discs, like DVD or Blu-ray disc, these methods and definitions of these signals are almost the same, in basic. For detailed information related to the optical storage, the readers may refer to the book "Optical Recording: A Technical Overview (Addison-Wesley, 1990)", U.S. Pat. No. 5,946,287 and U.S. Pat. No. 6,269,070.

For biomedical or biological applications, the size of the observed target or sample may range from nanometers to tens of microns and the retrieved image is supposed to have the resolution of at least several hundred nanometers. In this disclosure, the dimension of the address coding structure(s) in the address coding site should be smaller than 1 millimeter and may be varied according to the structural dimension of the sample. For encoding the sample of the size of cells, the size of the coding structure is required to be at least less than 100 micrometer, for example the size of mammalian cell around 10 to 50 micrometers. For observing the sample of the size of organelles, the size of the coding structure is required to be smaller than one micrometer.

Figure 17:
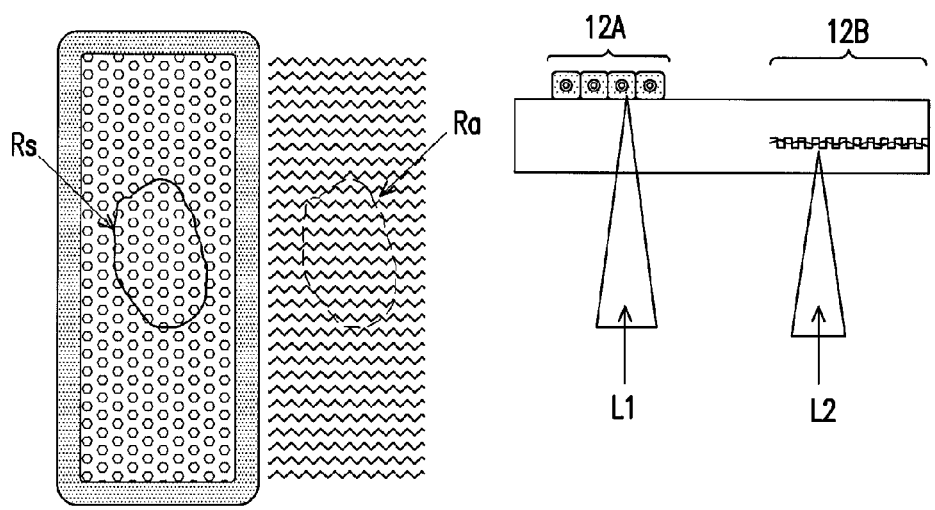
FIG. 17 shows schematic diagrams of the mapping between the regions of interest in the inspected site and in the address coding site as well as the scanning of both light beams toward both regions of the carrier.

FIG. 17 shows schematic diagrams of the mapping between the regions of interest in the inspected site and in the address coding site as well as the scanning of both light beams toward both sites. As shown in left part of FIG. 17, after selecting the region of interest (ROI) of the sample for image observation, the ROI of the sample Rs (marked by solid line) can be registered to the mapped ROI of the servo pattern Ra (marked by dotted line) of the address coding site through the servo mechanism of the optical device as described above. As shown in right part of FIG. 17, the light beam L1 of the sample inspecting device and the light beam L2 of the address detecting device are respectively focused on the inspected site 12A and the address coding site 12B, so that image capture from the inspected site 12A and address registration to the address coding site 12B are synchronized through the servo mechanism of the optical device as described above.

Figure 18:
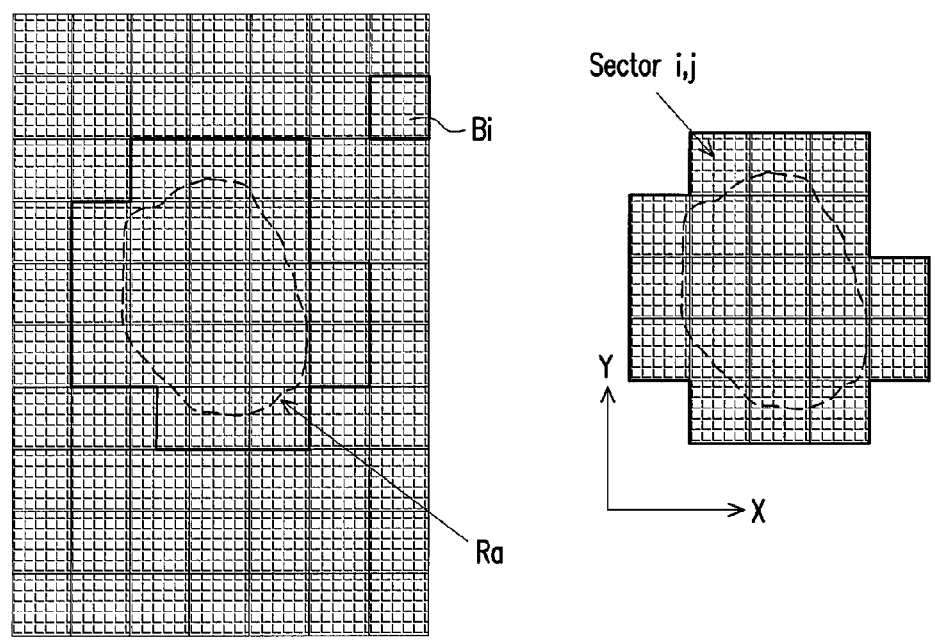
FIG. 18 shows the scanned range of the image sectors including the region of interest.

FIG. 18 shows the scanned range of the image sectors including the region of interest. As shown in FIG. 18, the mapped ROI of the servo pattern Ra (marked by dotted line) of the address coding site may be divided into a number of small blocks (i.e. address coding sector) Bi (marked by bold line) as image sectors (sectors (i, j)) to facilitate narrowing down the range of the image sectors required for capturing the ROI. That is, through the fine image sectors (i, j), it is possible to obtain the ROI only by scanning certain sectors (the scanned sectors marked in solid line), which helps the image capture more rapidly and more accurately.

Similar to the barcode principles, in order to address the captured image, each image sector may be defined as a variable sector, such as sector 1, sector 2, etc.; or as a sector with more than one variables, such as sector (1, 1), sector (1, 2) . . . and so on. The information of the sector codes or sector numbers are registered as micro-structures in the address coding sector, so as to provide at least two functions: (i) the image sector(s) of the address code(s) is recorded and (ii) the clock signal is provided as the time basis for the captured image pixel.

Specifically, the coding micro-structures in the address coding sector are encoded with sector codes (e.g. image sector numbers) of the address codes of the address coding site. And the clock signal for sampling the corresponding image signal(s) in the inspected site can be obtained by decoding the coding micro-structures.

This disclosure employs an optical detector built-in with an optical head (a pickup head). The optical detectors may be avalanche photodiodes (APD) or photo multiplier tubes (PMT), for example.

Figures 19, 20:
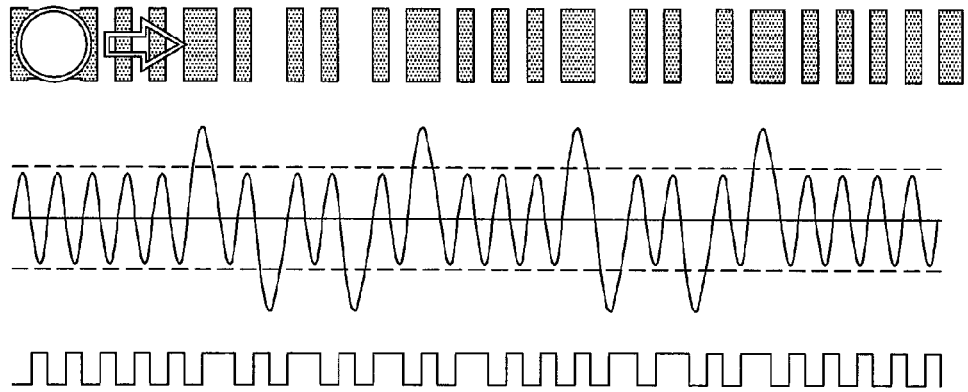
FIG. 19 shows the scanning direction of the light beam relative to the lands and grooves in the address coding sector and the sinusoidal waveform signal upon scanning.
FIG. 20 shows the division of the address coding site into a plurality of sectors with sector numbers.

FIG. 19 shows the scanning direction of the light beam relative to the lands and grooves in the address coding sector and the sinusoidal waveform signal upon scanning. As shown in FIG. 19, when a Gaussian beam incident on the address coding sector with lands and grooves (containing barcode signals), scanning along the direction (marked by the arrow) perpendicular to the extension direction of the grooves, signals of different intensity from different reflectivity of the lands and grooves are captured. The diffracted light of 0 order, +1 order and −1 order can be detected by the detector. Using the principles of constructive and destructive interferences to determine the optical head, the so-called push-pull tracking method, received by the quadrant detector, the push-pull signals based on different distances shifted from the center and the sinusoidal waveform signal (in the middle part of FIG. 19) are obtained. Alternatively, the sinusoidal waveform signal may be further converted to square waves (the bottom part of FIG. 19). Using the differences in the frequency and the amplitude of the received signals to decode the data of the current scanned address coding sector, i.e. sector (i, j). Additionally, the zero-cross of the push-pull signals can be used to generate the clock signals for accurately triggering the synchronized circuit(s), prompting the photo-detector to sample the image of the inspected site, (as shown in FIG. 19). Furthermore, the square waves (as shown in the bottom part of FIG. 19) can be transformed from the zero-cross of the push-pull signals firstly, then be used to obtain the periodical clock signals.

EXAMPLES OF ADDRESS CODING SITE

Example 1

The address coding sector, which is a part of the address coding site corresponding to the sample inspected site, may be divided into a plurality of small blocks (address coding sectors) as shown in FIG. 20, each block has a specific sector number: (X a, Y b), where X a represents a th block in X-direction, Y b represents b th block in Y-direction. Therefore, the sample inspected site may be divided into a plurality of inspected sectors with the same size of the corresponding address coding sector. When the device decodes the micro-structures and reads the data of address coding sector in the address coding site, at the same time, the device retrieves the image information of the sample region and a complete image is generated.

The micro-structures of the address coding sectors are encoded with the address codes corresponding to the sector numbers. Using the micro-structure of lands/grooves and "interleaved 2 of 5 code" as an example, it is shown in FIG. 21A-B, how the lands/grooves micro-structure encoded with "interleaved 2 of 5 code" barcodes is decoded by the optical equipment (including optical device, decoding module, and image generation module) to obtain the clock signal, the sector codes and further generate the images.

Figure 21A:
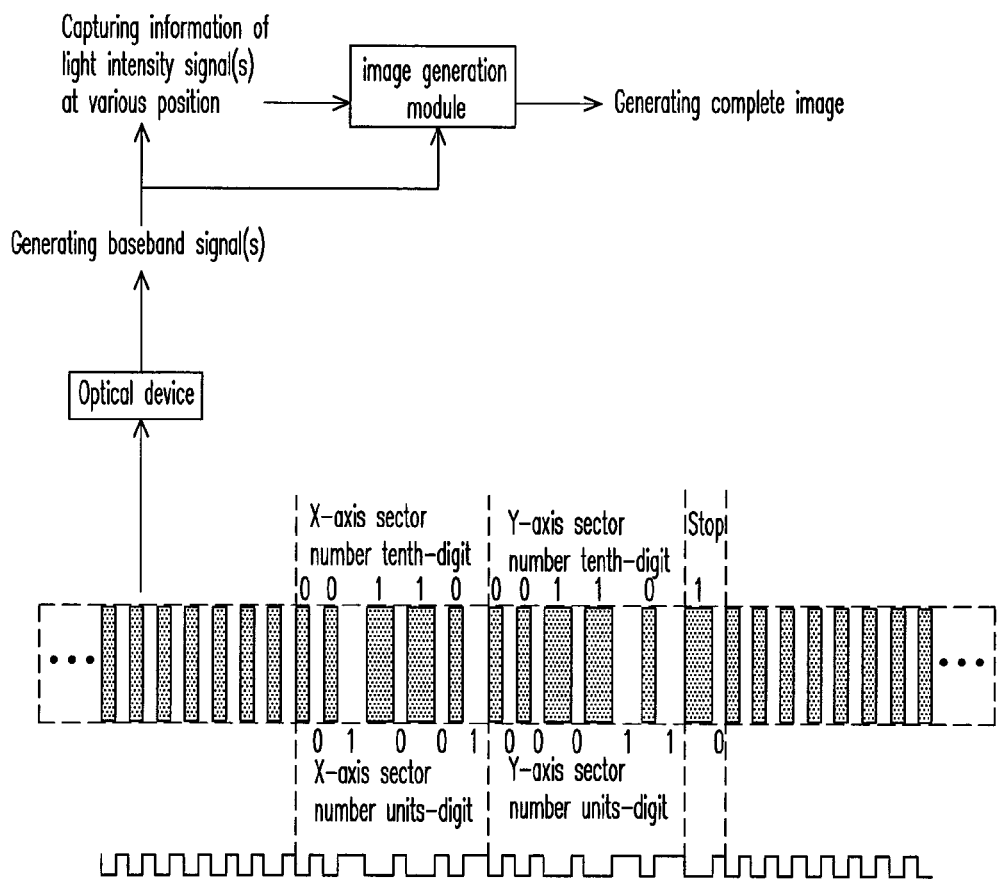
FIG. 21A shows the lands/grooves micro-structure encoded with the barcodes and decoding of the micro-structure for clock signal and capturing and generating images according to an embodiment of the disclosure.

FIG. 21A shows the lands/grooves micro-structure encoded with the barcodes and decoding of the micro-structure for clock signal, and capturing images according to an embodiment of the disclosure. The cross-sectional view (in FIG. 21A) and the top view (in FIG. 21A) of the micro-structures of the address coding sector are respectively shown in the lower part and middle part of FIG. 21A. The entire address coding sector is formed with linear parallel furrows to create a micro-structure of lands/grooves with a fixed period, similar to the grating. For an example of a carrier without address coding, the sampling image approach of a sample carrier is using one beam (L2 of FIG. 17) to scan the micro-structure of lands and grooves to generate a clock signal. According to the clock signal, another beam (L1 of FIG. 17) scans and samples the corresponding image signals in the sample inspected site. For another example of a carrier with address coding site, when light beam scans on the address coding sector, a clock signal with a specific frequency is obtained, and the clock signal can be used to trigger and sample the signals of light intensity received by the optical device at various positions in the inspected site.

Figure 21B:
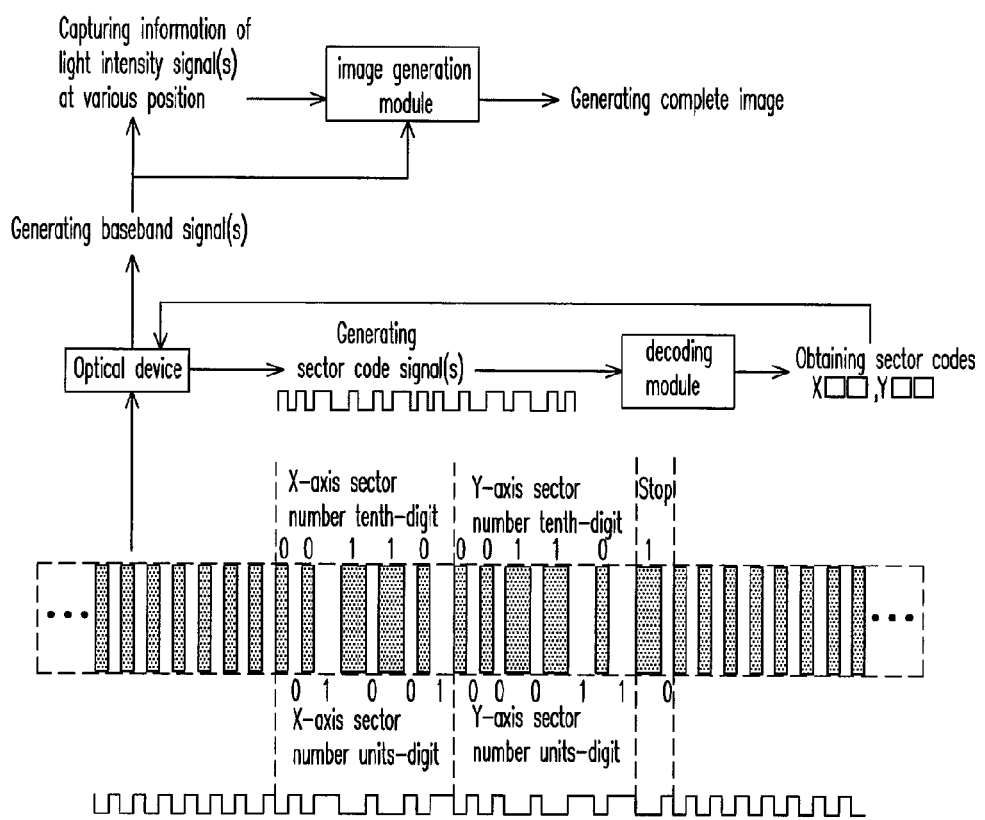
FIG. 21B shows the lands/grooves micro-structure encoded with the barcodes and decoding of the micro-structure for clock signal, sector codes and capturing and generating images according to an embodiment of the disclosure.

The cross-sectional view (in FIG. 21B) and the top view (in FIG. 21B) of the micro-structures of the address coding sector are respectively shown in the middle part and lower part of FIG. 21B. The entire address coding sector is formed with linear parallel furrows to create a micro-structure of lands/grooves with a fixed period, similar to the grating. When light beam scans on the address coding sector, a clock signal with a specific frequency is obtained, and the clock signal can be used to trigger and sample the signals of light intensity received by the optical device at various positions in the inspected site. For example, when the device decodes the micro-structures and reads the code data of the specific sector (X a, Y b) in the address coding site, at the same time, the device retrieves the image information in the sample inspected site. The image information corresponding to light intensity signals at various positions in the inspected site may be concatenated as an array into a complete image by the image generation module.

Figure 21C:
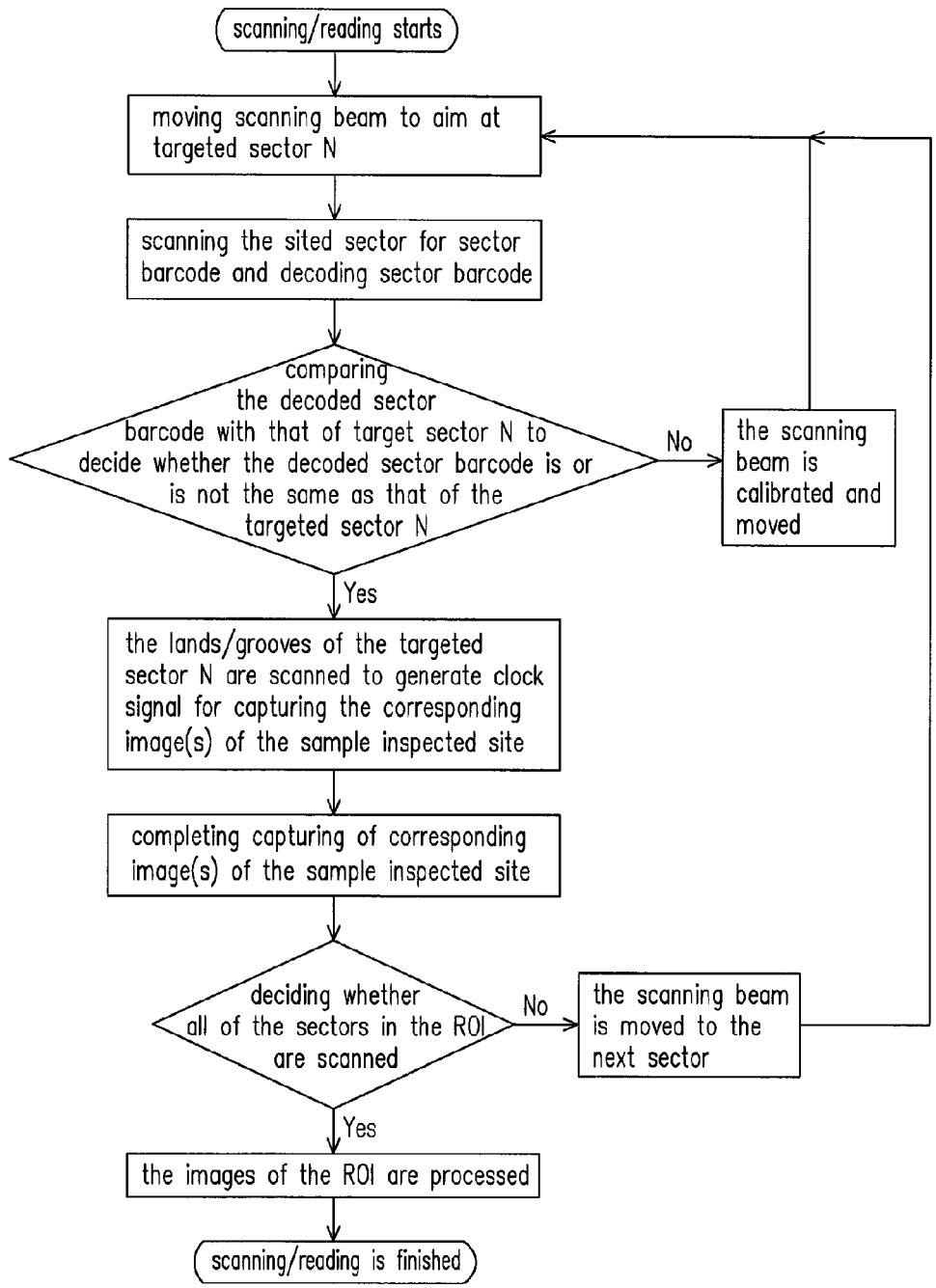
FIG. 21C shows a flowchart of an address registration method according to an embodiment of the disclosure.

FIG. 21C shows a flowchart of an address registration method according to an embodiment of the disclosure. Firstly, the scanning (i.e. reading) is started. Next, after a scanning beam is moved and aimed at a target address coding sector N of the address coding site, the sited address coding sector is scanned to decode the sector barcode data of the sited address coding sector. Then, the decoded sector barcode is compared with the sector barcode of the target address coding sector N, so as to decide whether the decoded sector barcode is the same as that of the target address coding sector N. When the decoded sector barcode is not the same as that of the target address coding sector N, the scanning beam is moved to target address coding sector by calculation. The position of the scanning may be fine-tuned to move a bit, so as to aim at the target address coding sector N again. When the decoded sector barcode is the same as that of the target address coding sector N, it means that the sited address coding sector is the target address coding sector N. Then, the target address coding sector N is read and lands/grooves of the target address coding sector N are scanned to generate clock signals for sampling and capturing the corresponding image signal(s) of the sample inspected site, and the corresponding image(s) of the sample in the inspected site is captured. After the capturing of the corresponding image(s) of the sample in the inspected site is completed, it is decided whether all of the sectors in the ROI are scanned. If not all of the sectors in the ROI are scanned, the scanning beam is moved to the next sector. If all of the sectors in the ROI are scanned, the images of the ROI are processed and generated. Then, the scanning is completed.

The disclosure is not limited by the above disclosed embodiments of the disclosure.

Figures 22A, 22B:
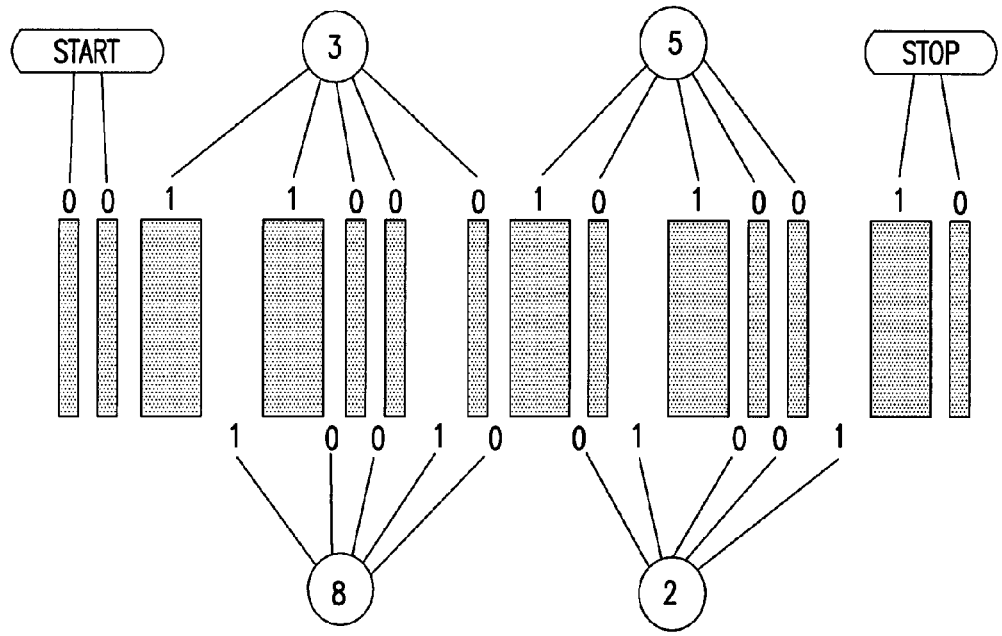
FIG. 22A is an example of codes of "interleaved 2 of 5 code".
FIG. 22B shows the symbol table of "interleaved 2 of 5 code".

FIG. 22A is an example of codes of "interleaved 2 of 5 code". Following the principles of "Interleaved 2 of 5 Code" in FIG. 22A, the land/groove micro-structures of the address coding sector in the address coding site as shown in the middle part of FIG. 21 can function as barcodes (i.e. the groove represents the black line and the land represents the white line, or groove represents the white line and the land represents the black line). The encoding rules as shown in FIG. 22A: a thick line represents bit "1" and a thin line represents bit "0", the Arabic numerals are represented by five bits composed of two thick black lines plus three thin black lines, or composed of the two thick white lines plus three thin white line. The staggered black and white lines barcodes represent a series of Arabic numerals. For example, the numeral "3" is represented by bits "11000" of the black lines, the numeral "8" is represented by bits "10010" of the white lines, the numeral "5" is represented by bits "10100" of the black lines, and the numeral "2" is represented by bits "01001" of the white lines. The "START" code is represented by bits "00" of the black lines, and the "END" code is represented by bits "10" of the black lines. FIG. 22B also shows the symbol table of "Interleaved 2 of 5 Code". In the figures, a thick line has a linewidth two or three times of the linewidth of the thin line, but the thickness of either thick or thin line is not limited by the examples as long as the thick or thin lines are distinguishable.

Herein, the encoding rules of the barcodes are not limited to the examples, and any kind of one-dimensional coding rules, such as: "Code 39", "Code 32", "Code 93", "Codabar", "Interleaved 2 of 5 code", "Industrial 2 of 5 Code", "Matrix 2 of 5 Code", "Code 11", "Code 128", China postal codes, UPC specified barcodes, EAN specified barcodes, ISBN specified barcodes, ISSN specified barcodes, MSI barcodes and etc., or their variants may be used as the addressing coding rule.

The micro-structures of the address coding site are not limited to the linear land/groove micro-structures. Alternatively, a pattern of light and dark stripes of a fixed period on the plane, similar to commercial barcode labels, is applicable as long as the device may scan and obtain a clock signal and address sector data.

Example 2

Figure 23:
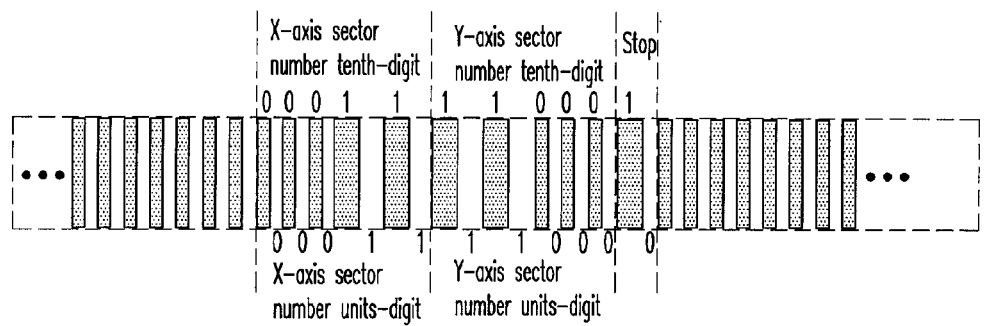
FIG. 23 shows a special case of eight adjacent thick lines aligned together when the sector number is (X77, Y33) for the barcodes.
Figure 24:
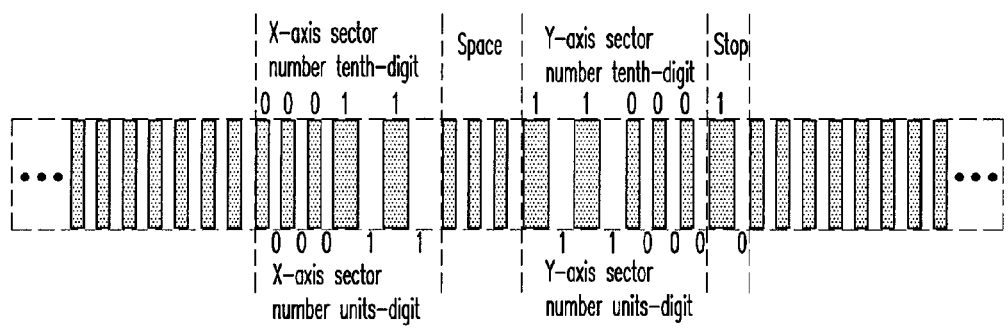
FIG. 24 shows a case of inserting a space region having a plurality of black and white constant lines between X- and Y-direction data barcode regions for the barcodes.

Following the principles of "Interleaved 2 of 5 Code", when the sector number is (X77, Y33), there will be a special case of eight adjacent thick lines (black and white lines) aligned together as shown in FIG. 23. The tenth-digit "7" in X direction is represented by bits "00011" of the black lines, the units-digit "7" in X direction is represented by bits "00011" of the white lines, the tenth-digit "3" in Y direction is represented by bits "11000" of the black lines, the units-digit "3" in Y direction is represented by bits "11000" of the white lines, and these symbols are concatenated together to form the string "00000011111111000000". As eight adjacent thick lines aligned together, errors maybe occur when generating the clock signals or decoding the address sector data. It is better to reduce the number of adjacent thick lines, and a space region having a plurality of black and white constant lines is inserted between the X-direction data barcode region and Y-direction data barcode region for separation purposes, as shown in FIG. 24, to avoid eight adjacent thick lines.

Example 3

Figure 25:
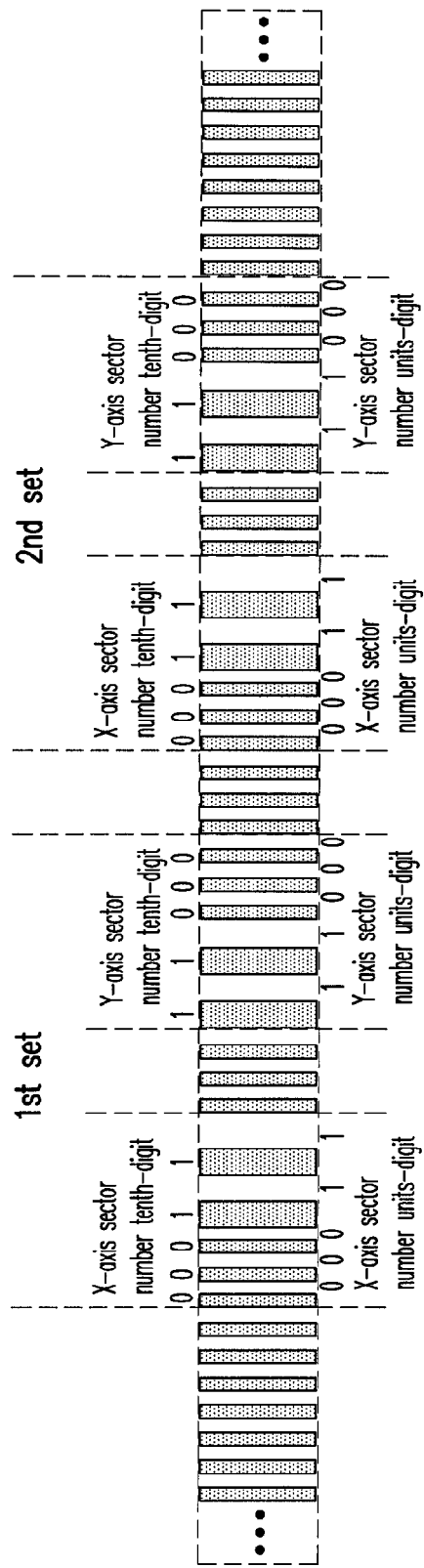
FIG. 25 shows a case of repeating the same set of data barcode regions for the barcodes.

In this embodiment, in order to avoid error reading of the sector number(s) owing to contamination or scratches occurred in the address coding sector, the same set of data barcode regions, including X-direction data barcode region, the space region and Y-direction data barcode region, may be repeated for several times. As shown in FIG. 25, the same set of data barcode regions are repeated twice to ensure the accuracy of data reading. If the sector numbers readout from the two sets of data barcode regions are not the same, it means that one of the two sets is erroneous, and the optical device should shift a small distance to re-read the sector number(s). Alternatively, the same set of data barcode regions may be repeated three times, and the correct sector number(s) to can be obtained when the readout results from at least two of the three sets are the same.

Example 4

Figure 26A:
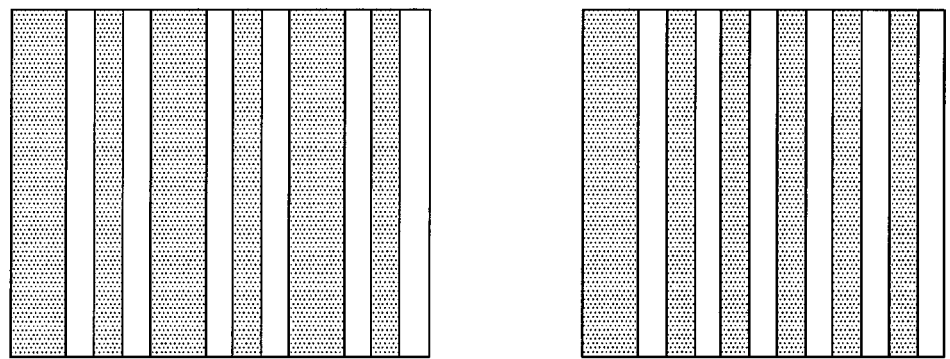
FIG. 26A is an example of binary codes of "0" and "1".

FIG. 26A is an example of binary codes of "0" and "1". As shown in FIG. 26A, the left and right address coding sectors correspond to binary digit signal data "0" and "1" for sequential coding. In the left part of FIG. 26A, the 12 black and white stripes represent the data "0", the black stripes 1, 5, 9 counted from the left are thick black stripes. In the right part of FIG. 26A, the 12 black and white stripes represent the data "1", the first black stripe counted from the left is a thick black stripe. In the present disclosure, the combinations of the stripes of the data, "0" and "1" for binary coding are not limited to combinations of this embodiment. Alternatively, the land/groove micro-structures may be used.

Figures 26B, 26C:
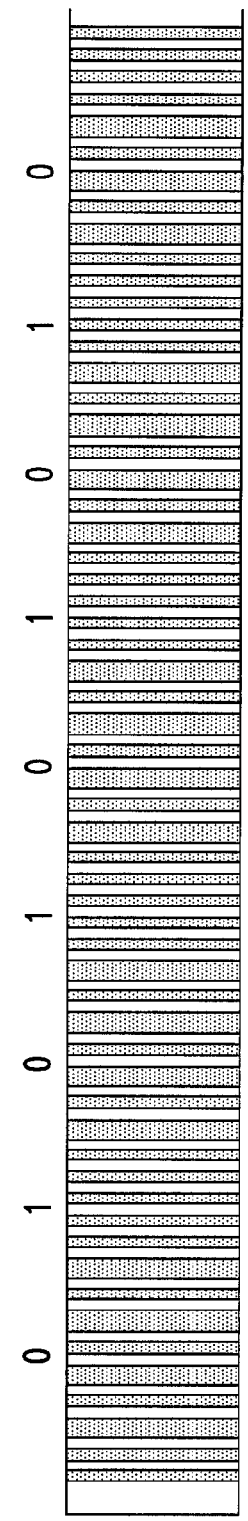
FIG. 26B shows the principle for assigning the address information of the address coding sector.
FIG. 26C shows the binary address patterns of the address coding sector of the block sector number (X5, Y5).

FIG. 26B shows the principle for assigning the address information of the address coding sector. The address information can be assigned in 4-bits sector numbers of the X-direction vs. 5-bits sector numbers of the Y-direction. Hence, the 4-bits sector numbers of X-direction encode 16 sector numbers (decimal number from 0 to 15), while the 5-bits sector numbers of Y-direction encode 32 sector numbers (decimal number from 0 to 31). FIG. 26C shows the binary address patterns of the address coding sector of the block sector number (X5, Y5).

Figures 27A, 27B, 27C:
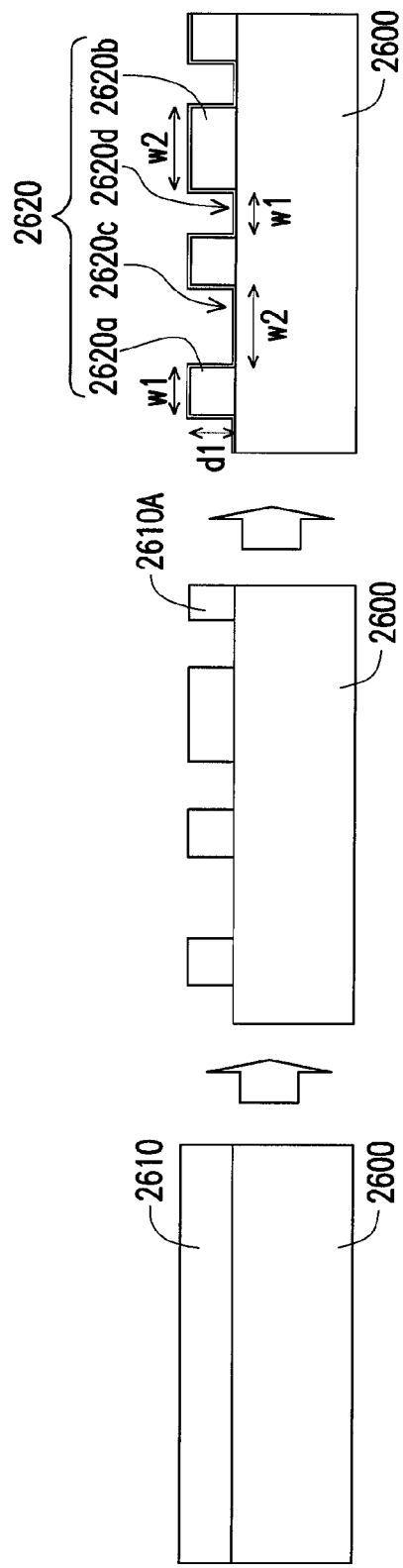
FIG. 27A-27C illustrates the fabrication process steps of the address coding site or address coding sector using photolithography.

The address coding sector or the address coding site for the captured image(s) can be formed with micro-structures fabricated by photolithography processes, nano-imprinting or injection molding. In one example, the address coding sector or the address coding site is fabricated by photolithography technology. As shown in FIGS. 27A-C, a substrate 2600, such as a silicon substrate, a glass substrate or a plastic substrate, is provided and coated with a positive-type photoresist layer 2610 of a thickness d1. The positive-type photoresist layer is exposed with a mask (not shown) having the encoding pattern therein under deep UV exposure and then developed to form a patterned positive-type photoresist layer 2610A with the encoding pattern. Finally, a metal reflective layer is formed to cover the patterned positive-type photoresist layer using vacuum sputtering or evaporation, so as to complete the address coding sector (in address coding site) 2620. The metal reflective layer may be made of gold, silver, aluminum or alloys thereof, for example. The address coding sector (in address coding site) 2620 may be further covered with a glass cover or laminated by another substrate if necessary.

In general, the address coding sector is formed with the micro-structure of a plurality of parallel grooves and a plurality of land sandwiched between the parallel grooves. The plurality of grooves and the plurality of lands are arranged in alternation. Each of the plurality of lands is located between any two most adjacent grooves of the plurality of grooves. The widths of the plurality of grooves may be the same or different, while the widths of the plurality of lands may be the same or different.

As shown in the cross-sectional view of FIG. 27C, the address coding sector 2620 includes at least a first land 2620a of a first width w1 and a second land 2620b of a second width w2, a first groove 2620c of the second width w2 and a second groove 2620d of the first width w1. $\lambda$ is the wavelength of light reading or scanning the address coding sector. If the thickness d1 of the photoresist layer is about ¼ of the wavelength $\lambda$ (i.e. d1≈$\lambda$/4), better cross-track signals may be obtained for the optical device scanning the address coding sector. For example, the thickness d1 is about 160 nm, the widths w1 and w2 are respectively 350 nm and 700 nm when $\lambda$ is 650 nm. If the thickness d1 of the photoresist layer is about ⅛~⅙ of the wavelength $\lambda$ (i.e. d1≈$\lambda$/8~$\lambda$/6), better push-pull signals may be obtained for the optical device scanning the address coding sector.

Alternatively, the photoresist material may be positive or negative photoresist materials, and the micro-structures formed in the address coding sector may be designed with lands and grooves with various widths. It is understood that the manufacturing processes, the material or the design of the coding sector(s) are not limited to the examples described above.

The carrier mentioned in this disclosure may be a test slide or an assay plate, such as pathology slides, cell culture chamber slides, a microfluidic chip or plate or a microtiter plate (also called as microplate or microwell plate). Through the design of placing the address coding site on or in the carrier (slide or microplate) for carrying the sample, the absolute address or coordinates of the sample on the carrier can be provided in reference to the address coding sector and recorded by the optical scanning device, which is beneficial for multiple scanning of the same slide or carrier at different time. In this way, it is easy to return to any region of interest (ROI) for repeated observations and recordings. When switching between different platforms of the optical device, the region of interest can also be quickly retrieved by inputting the absolute address or coordinates of the sample on the carrier.

As the address coding site is formed on or in the carrier (slide or microplate), the carrier for carrying a sample offers the optical registration function, allowing the registration of inspected results of the sampling points of the sample to the corresponding address codes of the address coding sector in address coding site of the carrier.

Figure 28A:
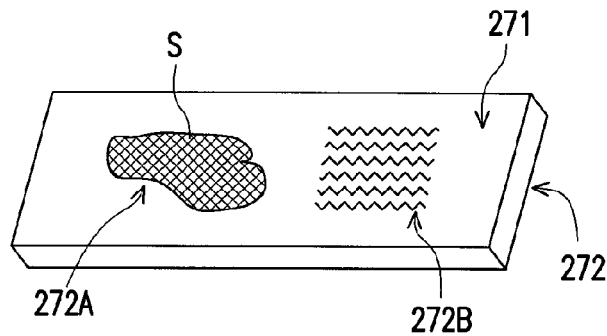
FIG. 28A-28B show different types of carriers with inspected site(s) and address coding site(s).
Figure 28B:
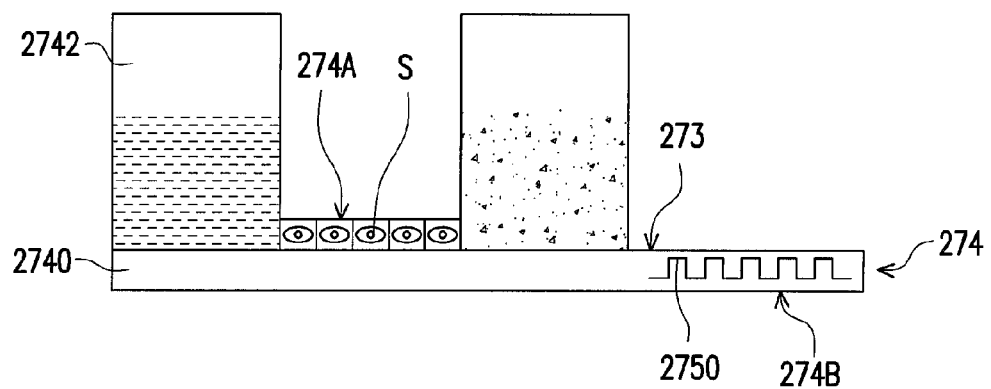

Regarding the location of the address coding site of the carrier, it is not necessary to have the inspected site and the address coding site on the same focal plane. FIGS. 28A-28B show different types of carriers with inspected site(s) and address coding site(s). As shown in FIG. 28A, the inspected site 272A for carrying the sample S (such as tissue slices) and the address coding site 272B are located on the same surface (the same focal plane) 271 of the slide 272. Alternatively, in FIG. 28B, the slide 274 includes a body 2740 with at least one cell culture chamber 2742 mounted thereon. The sample S (such as cultivated cells) is located on the top surface 273 of the slide 274 and within the inspected site 274A. However, the address coding micro-structures 2750 are embedded within the body 2740 of the slide 274, and the address coding site 274B is located on a focal plane different to that of the inspected site 274A.

Figure 29:
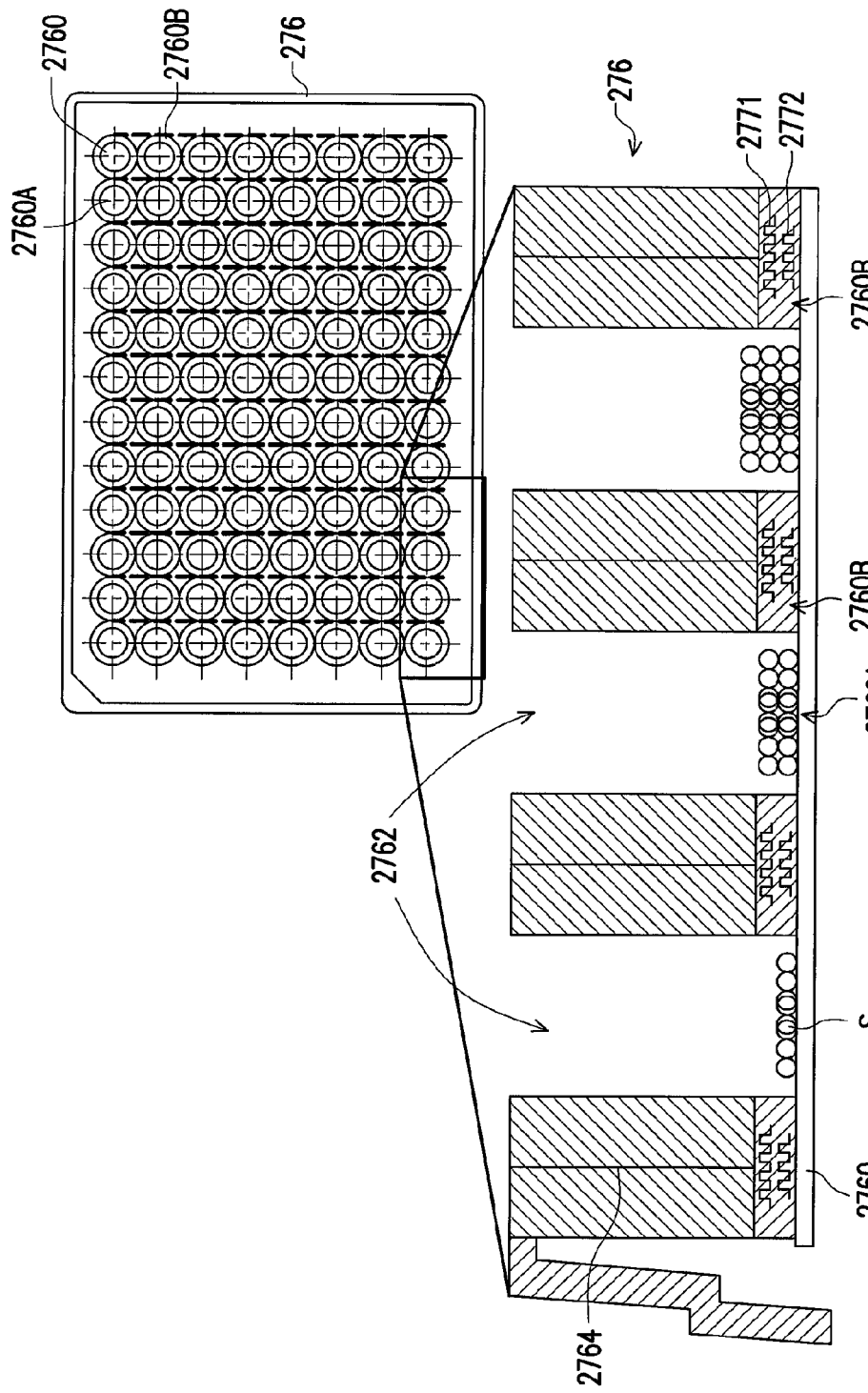
FIG. 29 shows schematic diagrams of a microtiter plate having the address coding sites on different focal planes.

FIG. 29 shows schematic diagrams of bottom view and a cross-sectional view of a microtiter plate having the address coding sites on different focal planes. In another example, as shown in FIG. 29, the carrier is a microtiter plate 276 having a body 2760 and a plurality of micro-wells 2762 mounted thereon. The sample S is loaded within the round micro-wells 2762, and the inspected sites 2760A for carrying the sample S are encircled by the micro-wells 2762. The address coding sites 2760B are located within the adjacent areas 2764 of the micro-wells 2762 and located at a bottom part of the adjacent areas 2764. The address coding site 2760B includes a first address coding site 2771 and a second address coding site 2772 located at different focal planes and embedded within the adjacent areas 2764 of the micro-wells 2762.

It is possible to have the inspected site and the address coding site located on two different focal planes. It is also possible to have one or more address coding sites located on different focal planes or on the focal plane different to that of the inspected site. While the address detecting device focuses on the address coding sites of different focal planes for address registration, the sample inspecting device also focuses on different positions of the sample on different focal planes, thus implementing layered scanning of the sample structure and reconstructing the three-dimensional structure of the sample.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A carrier for carrying a sample, comprising:
   a body of the carrier;
   an inspected site on the body, wherein the sample is carried on the inspected site;
   an address coding site, wherein the address coding site includes at least one coding micro-structure located in the body or located on the body, and a dimension of the coding micro-structure is at least less than 100 microns, wherein a plurality of sampling images captured at a plurality of locations of the inspected site correspond to a plurality of address codes detected at a plurality of locations of the address coding site, and all of relative positions between the locations of the inspected site and the corresponding locations of the address coding site are the same.

2. The carrier of claim 1, wherein the address coding site includes at least one address coding sector.

3. The carrier of claim 1, wherein the at least one coding micro-structure of the address coding site is encoded with sector codes.

4. The carrier of claim 3, wherein an encoding rule of the at least one coding micro-structure is selected from one of coding rules of barcode systems.

5. The carrier of claim 1, wherein a clock signal is generated by scanning the at least one coding micro-structure in the address coding site and the clock signal for sampling the corresponding image in the inspected site.

6. The carrier of claim 1, wherein the at least one coding micro-structure includes a plurality of grooves and a plurality of lands arranged in alternation, the plurality of grooves is parallel to each other and each of the plurality of lands is located between any two most adjacent grooves of the plurality of grooves.

7. The carrier of claim 6, wherein the plurality of grooves includes at least a first groove of a first width and/or at least a second groove of a second width.

8. The carrier of claim 6, wherein the plurality of lands includes at least a first land of a first width and/or at least a second land of a second width.

9. The carrier of claim 1, wherein the carrier further includes at least one cell culture chamber mounted on the body, the inspected site is located within the at least one cell culture chamber, the address coding site is located in the body, so that the inspected site and the address coding site are located on different focal planes.

10. A carrier for carrying a sample, comprising:
    a plurality of inspected sites on a surface of the carrier, wherein samples are carried on the plurality of inspected sites;
    a plurality of address coding sites, wherein the plurality of address coding sites and the plurality of inspected sites are arranged in alternation;
    wherein a plurality of sampling images captured at a plurality of locations of the inspected site correspond to a plurality of address codes detected at a plurality of locations of the address coding site, and all of relative positions between the locations of the inspected site and the corresponding locations of the address coding site are the same.

11. The carrier of claim 10, further comprising a plurality of micro-wells mounted on a body and correspondingly encircled the plurality of the inspected sites, wherein the plurality of the address coding sites is located in/on adjacent areas of the plurality of micro-wells.

12. The carrier of claim 11, wherein each of the plurality of the address coding sites includes a first address coding site and a second address coding site located on different focal planes and embedded in/on the adjacent areas of the plurality of the micro-wells.

13. The carrier of claim 12, wherein the first or second address coding site includes at least one coding micro-structure located in/on the adjacent areas of the plurality of the micro-wells, and the at least one coding micro-structure of the first or second address coding site is encoded with sector codes.

14. The carrier of claim 13, wherein an encoding rule of the at least one coding micro-structure is selected from one of coding rules of barcode systems.

15. The carrier of claim 13, wherein a clock signal is generated by scanning the at least one coding micro-structure in the first and second address coding site and the clock signal for sampling the corresponding for image in the inspected site.

16. The carrier of claim 13, wherein the at least one coding micro-structure includes a plurality of grooves and a plurality of lands arranged in alternation, the plurality of grooves is parallel to each other and each of the plurality of lands is located between any two most adjacent grooves of the plurality of grooves.

17. The carrier of claim 16, wherein the plurality of grooves includes at least a first groove of a first width and/or at least a second groove of a second width.

18. The carrier of claim 16, wherein the plurality of lands includes at least a first land of the first width and/or at least a second land of the second width.

* * * * *